US008080260B2

(12) United States Patent
Derwin et al.

(10) Patent No.: US 8,080,260 B2
(45) Date of Patent: Dec. 20, 2011

(54) MOLECULAR ENHANCEMENT OF EXTRACELLULAR MATRIX AND METHODS OF USE

(75) Inventors: Kathleen Anne Derwin, Shaker Heights, OH (US); Joseph Patrick Iannotti, Strongsville, OH (US); LiKang Chin, Cleveland, OH (US); Anthony Calabro, Cleveland Heights, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 484 days.

(21) Appl. No.: 12/378,296

(22) Filed: Feb. 13, 2009

(65) Prior Publication Data
US 2009/0204227 A1 Aug. 13, 2009

Related U.S. Application Data

(60) Provisional application No. 61/065,527, filed on Feb. 13, 2008.

(51) Int. Cl.
*A61B 17/08* (2006.01)
*A61F 2/02* (2006.01)

(52) U.S. Cl. ........ 424/423; 424/426; 424/484; 424/488; 525/54.1; 525/54.2; 525/326.1; 525/420; 525/540; 623/11.11; 623/13.11

(58) Field of Classification Search .................. 424/423, 424/426, 484, 488; 525/54.1, 54.2, 326.1, 525/420, 540; 623/11.11, 13.11
See application file for complete search history.

(56) References Cited

U.S. PATENT DOCUMENTS

| 4,024,073 | A | 5/1977 | Shimizu et al. |
| 4,256,596 | A | 3/1981 | Cohen |
| 4,277,582 | A | 7/1981 | Mueller et al. |
| 4,350,629 | A | 9/1982 | Yannas et al. |
| 4,500,676 | A | 2/1985 | Balazs et al. |
| 5,017,229 | A | 5/1991 | Burns et al. |
| 5,532,221 | A | 7/1996 | Huang et al. |
| 5,667,778 | A | 9/1997 | Atala |
| 5,705,488 | A | 1/1998 | Janzen et al. |

(Continued)

FOREIGN PATENT DOCUMENTS

EP 0 516026 A1 12/1992

(Continued)

OTHER PUBLICATIONS

Aeschbach, R., Amado, R. and Neukom, H., "Formation of Dityrosine Cross-Links in Proteins by Oxidation of Tyrosine Residues," Biochimica et Biophysica Acta, Protein Structure, vol. 439, No. 1, pp. 292-301, 1976.

(Continued)

*Primary Examiner* — Irina S Zemel
(74) *Attorney, Agent, or Firm* — Pearne & Gordon LLP

(57) ABSTRACT

A composition comprising a human- or animal-derived extracellular matrix and a macromolecular network which is prepared ex vivo is provided that is useful in the repair of a tissue injury, particularly in repair of tears or gaps between a tendon and a bone, such as in a rotator cuff tear. In an embodiment, the composition comprises a human- or animal-derived extracellular matrix having impregnated therein a macromolecular network of hyaluronan macromolecules that have been cross-linked via dihydroxyphenyl linkages, so that the cross-linked network is interlocked within the extracellular matrix. The resulting HA-incorporated extracellular matrix can be supplied in the form of a patch to reinforce a tissue repair or cover a tissue defect.

28 Claims, 6 Drawing Sheets
(2 of 6 Drawing Sheet(s) Filed in Color)

U.S. PATENT DOCUMENTS

| | | | |
|---|---|---|---|
| 5,739,113 | A | 4/1998 | Lee |
| 5,769,899 | A | 6/1998 | Schwartz et al. |
| 5,976,526 | A | 11/1999 | Atala |
| 6,060,053 | A | 5/2000 | Atala |
| 6,251,876 | B1 | 6/2001 | Bellini et al. |
| 6,586,493 | B1 | 7/2003 | Massia et al. |
| 6,982,298 | B2 | 1/2006 | Calabro et al. |
| 7,060,287 | B1 | 6/2006 | Hubbard et al. |
| 7,157,080 | B2 | 1/2007 | Radice et al. |
| 7,368,502 | B2 | 5/2008 | Calabro et al. |
| 7,465,766 | B2 | 12/2008 | Calabro et al. |
| 2001/0027237 | A1 | 10/2001 | Mayes et al. |
| 2004/0047892 | A1 | 3/2004 | Desrosiers et al. |
| 2004/0063206 | A1 | 4/2004 | Rowley et al. |
| 2004/0127698 | A1 | 7/2004 | Tsai et al. |
| 2004/0185021 | A1 | 9/2004 | Hubbard |
| 2005/0065616 | A1 | 3/2005 | Ankorina-Stark et al. |
| 2006/0040894 | A1 | 2/2006 | Hunter et al. |
| 2006/0040895 | A1 | 2/2006 | Thacker |
| 2007/0014729 | A1 | 1/2007 | Farhat et al. |
| 2009/0305983 | A1 | 12/2009 | Ying et al. |

FOREIGN PATENT DOCUMENTS

| | | |
|---|---|---|
| EP | 0 718312 A2 | 6/1996 |
| EP | 1 312383 A2 | 5/2003 |
| JP | 54-36388 | 3/1979 |
| JP | 7-102002 | 4/1995 |
| JP | 8-85703 | 4/1996 |
| JP | 09-059303 A | 3/1997 |
| JP | 2000-041691 A | 2/2000 |
| JP | 2001-097908 A | 4/2001 |
| JP | 2002-80501 | 3/2002 |
| JP | 2003-10308 | 1/2003 |
| WO | 85/04413 A1 | 10/1985 |
| WO | 89/02445 A1 | 3/1989 |
| WO | 89/07426 A1 | 8/1989 |
| WO | 90/09769 A1 | 9/1990 |
| WO | 93/07862 A1 | 4/1993 |
| WO | 97/18244 A1 | 5/1997 |
| WO | 99/57301 A1 | 11/1999 |
| WO | 00/01733 A1 | 1/2000 |
| WO | 00/16818 A1 | 3/2000 |
| WO | 00/37124 A1 | 6/2000 |
| WO | 00/46252 A1 | 8/2000 |
| WO | 00/54762 A2 | 9/2000 |
| WO | 01/00792 A1 | 1/2001 |
| WO | 01/85845 A1 | 11/2001 |
| WO | 02/18450 A1 | 3/2002 |
| WO | 02/060375 A2 | 8/2002 |
| WO | 02/068383 A2 | 9/2002 |
| WO | 03/006068 A1 | 1/2003 |
| WO | 03/007879 A2 | 1/2003 |
| WO | 03/018033 A1 | 3/2003 |
| WO | 03/018044 A1 | 3/2003 |
| WO | 03/061626 A1 | 7/2003 |
| WO | 03/072157 A1 | 9/2003 |
| WO | 03/076475 A1 | 9/2003 |
| WO | 2004/050712 A1 | 6/2004 |
| WO | 2006/101885 A2 | 9/2006 |
| WO | 2007/097710 A1 | 8/2007 |

OTHER PUBLICATIONS

Akkara, J.A., Senecal, K.J. and Kaplan, D.L., "Synthesis and Characterization of Polymers Produced by Horseradish Peroxidase in Dioxane," J. Polymer Science, Polymer Chemistry, vol. 29, pp. 1561-1574, 1991.

Allemann, F., Mizuno, S., Eid, K., Yates, K.E., Zaleske, D. and Glowacki, J., "Effects of hyaluronan on engineered articular cartilage extracellular matrix gene expression in 3-dimensional collagen scaffolds," J. Biomed. Mater. Res., vol. 55, No. 1, pp. 13-19, Apr. 2001.

Anderson, Svend Olav, "Cross-links in resilin identified as dityrosine and trityrosine," Biochimica et Biophysica Acta, General Subjects, vol. 93, No. 1, pp. 213-215, XP002363818, Copenhagen, 1964.

Anderson, Svend Olav, "Regional differences in degree of resilin cross-linking in the desert locust, Schistocerca gregaria," Insect Biochemistry and Molecular Biology 34, pp. 459-466, 2004.

Aslam, M. and Dent A., Bioconjugation: Protein Coupling Techniques for the Biomedical Sciences, Chapters 5 and 6, pp. 216-482, Macmillan Reference Ltd., London, UK, 1998.

Aurora, A., McCarron, J., Iannotti, J.P. and Derwin, K., "Commercially available extracellular matrix materials for rotator cuff repairs: state of the art and future trends," J. Shoulder Elbow Surg., vol. 16, No. 5S, pp. S171-S178, Sep. 2007.

Badhe, S.P., Lawrence, T.M., Smith, F.D. and Lunn, P.G., "An assessment of porcine dermal xenograft as an augmentation graft in the treatment of extensive rotator cuff tears," J. Shoulder Elbow Surg., vol. 17, No. 1S, pp. 35S-39S, Jan. 2008.

Badylak, S.F., "The extracellular matrix as a scaffold for tissue reconstruction," Semin. Cell. Dev. Biol., vol. 13, No. 5, pp. 377-383, 2002.

Badylak, S.F., "Xenogeneic extracellular matrix as a scaffold for tissue reconstruction," Transplant Immunology, vol. 12, pp. 367-377, 2004.

Bedrossian, Jr., E.H., "Banked fascia lata as an orbital floor implant," Opthalmic Plast. Reconstr. Surg., vol. 9, No. 1, pp. 66-70, 1993.

Blumenkrantz, N. and Asboe-Hansen, G., "New method for quantitative determination of uronic acids," Anal. Biochem. 54, pp. 484-489, 1973.

Bright, R.W. and Green, W.T., "Freeze-dried fascia lata allografts: a review of 47 cases," J. Pediatr. Orthop., vol. 1, No. 1, pp. 13-22, 1981.

Brittberg, M., Lindahl, A., Nilsson, A., Ohlsson, C., Isaksson, O., and Peterson, L., "Treatment of deep cartilage defects in the knee with autologous chondrocyte transplantation," N. Engl. J. Med. 331, pp. 889-895, 1994.

Brown, A.L., Srokowski, E.M., Shu, X.Z., Prestwich, G.D. and Woodhouse, K.A., "Development of a model bladder extracellular matrix combining disulfide cross-linked hyaluronan with decellularized bladder tissue," Macromol. Biosci., vol. 6, No. 8, pp. 648-657, Aug. 2006.

Buckwalter, J.A. and Mankin, H.J., "Articular cartilage: Degeneration and osteoarthrosis, repair, regeneration, and transplantation," J. Bone Joint Surgery [Am] 79A, pp. 612-632, 1997.

Bulpitt, P. and Aeschlimann, D., "New strategy for chemical modification of hyaluronic acid: Preparation of functionalized derivatives and their use in the formation of novel biocompatible hydrogels," J. Biomed. Mater. Res. 47, pp. 152-169, 1999.

Burkhead, W.Z., Schiffern, S.C. and Krishnan, S.G., "Use of Graft Jacket as an augmentation for massive rotator cuff tears," Semin Arthro., vol. 18, pp. 11-18, 2007.

Calabro, A., Benavides, M., Tammi, M., Hascall, V.C., and Midura, R.J., "Microanalysis of enzyme digests of hyaluronan and chondroitin/dermatan sulfate by fluorophore-assisted carbohydrate electrophoresis (FACE)," Glycobiology 10, pp. 273-281, 2000.

Calabro, A., Hascall, V.C., and Midura, R.J., "Adaptation of FACE methodology for microanalysis of total hyaluronan and chondroitin sulfate composition from cartilage," Glycobiology 10, pp. 283-293, 2000.

Darr, A. and Calabro, A., "Synthesis and characterization of tyramine-based hyaluronan hydrogels," J. Mater. Sci.: Mater. Med., vol. 20, No. 1, pp. 33-44, Jan. 2009.

De La Motte, C.A., Hascall, V.C., Calabro, A., Yen-Lieberman, B. and Strong, S.A., "Mononuclear leukocytes preferentially bind via CD44 to hyaluronan on human intestinal mucosal smooth muscle cells after virus infection or treatment with poly(I:C)," J. Biol. Chem. 274, pp. 30747-30755, 1999.

Derwin, K.A., Baker, A.R., Spragg, R.K., Leigh, D.R., Farhat, W. and Iannotti, J.P., "Regional variability, processing methods, and biophysical properties of human fascia lata extracellular matrix," J. Biomed. Mater. Res., Part A, vol. 84, No. 2, pp. 500-507, Feb. 2008.

Dopirak, R., Bond, J.L. and Snyder, S.J., "Arthroscopic total rotator cuff replacement with an acellular human dermal allograft matrix," Intl. J. Shoulder Surg., vol. 1, No. 1, pp. 7-15, Jan. 2007.

Fitzgerald, M.P., Mollenhauer, J., Bitterman, P. and Brubaker, L., "Functional failure of fascia lata allografts," Am. J. Obstet. Gynecol., vol. 181, No. 6, pp. 1339-1344, Dec. 1999.

Funakoshi, T., Majima, T., Iwasaki, N. Suenaga, N., Sawaguchi, N., Shimode, K., Minami, A., Harada K. and Nishimura, S., "Application of tissue engineering techniques for rotator cuff regeneration using a chitosan-based hyaluronan hybrid fiber scaffold," Am. J. Sports Med., vol. 33, No. 8, pp. 1193-1201, 2005.

Ghosh, K., Ren, X.D., Shu, X.Z., Prestwich, G.D. and Clark, R.A.F., "Fibronectin functional domains coupled to hyaluronan stimulate adult human dermal fibroblast responses critical for wound healing," Tissue Eng., vol. 12, No. 3, pp. 601-613, 2006.

Gross, A.J., "The oxidation of tyramine and related compounds by peroxidase," Ph.D. Thesis, MIT, pp. 1-84, 1954.

Gross, A.J. and Sizer, I.W., "The Oxidation of Tyramine, Tyrosine and Related Compounds by Peroxidase," Dept. of Biology, MIT, vol. 234, No. 6, pp. 1611-1614, 1959.

Haas, F., Seibert, F.J., Koch, H., Hubmer, M., Moshammer, H.E., Pierer, G. and Scharnagl, E., "Reconstruction of combined defects of the Achilles tendon and the overlying soft tissue with a fascia lata graft and a free fasciocutaneous lateral arm flap," Ann. Plast. Surg., vol. 51, No. 4, pp. 376-382, Oct. 2003.

Hagberg, L. and Gerdin, B., "Sodium hyaluluronate as an adjunct in adhesion prevention after flexor tendon surgery in rabbits," J. Hand Surg. [Am.], vol. 17A, No. 5, pp. 935-941, Sep. 1992.

Hu, M., Sabelman, E.E., Cao, Y., Chang, J. and Hentz, V.R., "Three-dimensional hyaluronic acid grafts promote healing and reduce scar formation in skin incision wounds," J. Biomed. Mater. Res. Part B: Appl. Biomater., vol. 67, No. 1, pp. 586-592, Oct. 2003.

Hunziker, E.B. and Rosenberg, L.C., "Repair of partial-thickness defects in articular cartilage: Cell recruitment from the synovial membrane," J. Bone Joint Surgery [Am] 78A, pp. 721-733, 1996.

Iannotti, J.P., Antoniou, J., Williams, G.R. and Ramsey, M.L., "Iliotibial band reconstruction for treatment of glenohumeral instability associated with irreparable capsular deficiency," J. Shoulder Elbow Surg., vol. 11, No. 6, pp. 618-623, Nov. 2002.

Iannotti, J.P., Codsi, M.J., Kwon, Y.W., Derwin, K., Ciccone, J. and Brems, J.J., "Porcine small intestine submucosa augmentation of surgical repair of chronic two-tendon rotator cuff tears: a randomized, controlled trial," J. Bone Joint Surg. [Am.], vol. 88, No. 6, pp. 1238-1244, Jun. 2006.

Ishii, T., "Structure and functions of feruloylated polysaccharides," Plant Science, vol. 127, pp. 111-127, 1997.

Jurvelin, J.S., Buschmann, M.D. and Hunziker, E.B., "Optical and mechanical determination of Poisson's ratio of adult bovine humeral articular cartilage," J. Biomech. 30(3), pp. 235-241, 1997.

Kalra, B., Kumar, A. and Gross, R.A., "Gel formation by enzyme-selected crosslinking of tyramine decorated poly(aspartamide)," Polymer Preprints 2000, 41(2), pp. 1804-1805, 2000.

Moro-Oka, T., Miura, H., Mawatari, T., Kawano, T., Nakanishi, Y., Higaki, H. and Iwamoto, Y., "Mixture of hyaluronic acid and phospholipid prevents adhesion formation on the injured flexon tendon in rabbits," J. Orthop. Res., vol. 18, No. 5, pp. 835-840, Sep. 2000.

Mow, V.C., Kuei, S.C., Lai, W.M. and Armstrong, C.G., "Biphasic creep and stress relaxation of articular cartilage in compression: theory and experiments," J. Biomech. Engin. 102, pp. 73-84, 1980.

Pouyani, T., Kuo, J.W., Harbison, G.S. and Prestwich, G.D., "Solid-state NMR of N-acylureas derived from the reaction of hyaluronic acid with isotopically-labeled carbodiimides," J. Am. Chem. Soc., 114, pp. 5972-5976, 1992.

Schimizzi, A.L., Massie, J.B., Murphy, M., Perry, A., Kim, C.W., Garfin, S.R. and Akeson, W.H., "High-molecular-weight hyaluronan inhibits macrophage proliferation and cytokine release in the early wound of a preclinical postlaminectomy rat model," Spine J., vol. 6, No. 5, pp. 550-556, Sep. 2006.

Sehgal, D. and Vijay, I.K., "A method for the high efficiency of water-soluble carbodiimide-mediated amidation," Anal. Biochem. 218, pp. 87-91, 1994.

Shu, X.Z., Ahmad, S., Liu, Y. and Prestwich, G.D., "Synthesis and evaluation of injectable, in situ crosslinkable synthetic extracellular matrices for tissue engineering," J. Biomed. Mater. Res. A., vol. 79, No. 4, pp. 902-912, Dec. 2006.

Sikka, R.S., Neault, M. and Guanche, C.A., "Reconstruction of the pectoralis major tendon with fascia lata allograft," Orthopedics, vol. 28, No. 10, pp. 1199-1202, Oct. 2005.

Sofia, S.J., Singh, A. and Kaplan, D.L., "Peroxidase-Catalyzed Crosslinking of Functionalized Polyaspartic Acid Polymers," J. Macromolecular Science, Pure and Applied Chemistry, vol. A39, No. 10, pp. 1151-1181, 2002.

Soltz, M.A. and Ateshian, G.A., "A conewise linear elasticity mixture model for the analysis of tension-compression nonlinearity in articular cartilage," J. Biomech. Engin. 122, pp. 576-586, 2000.

Thornton, T.D. and Savage, P.E., "Phenol oxidation pathways in supercritical water," Industrial & Engineering Chemistry Research, vol. 31, pp. 2451-2456, XP002363819, 1992.

Tomihata, K. and Ikada, Y., "Crosslinking and degradation of biopolymer," Recent Res. Devel. Biotech. & Bioeng., vol. 4, pp. 35-49, 2001.

Valentin, J.E., Badylak, J.S., McCabe, G.P. and Badylak, S.F., "Extracellular matrix bioscaffolds for orthopaedic applications: a comparative histologic study," J. Bone Joint Surg. [Am.], vol. 88, No. 12, pp. 2673-2686, Dec. 2006.

Wells-Knect, M., Huggins, T.G., Dyer, D.G., Thorpe, S.R. aAnd Baynes, J.W., "Oxidized Amino Acids in Lens Protein with Age," J. Biol. Chem., vol. 268, No. 17, pp. 12348-12352, 1993.

Whitlock, P.W., Smith, T.L., Poehling, G.G., Shilt, J.S. and Van Dyke, M., "A naturally derived, cytocompatible, and architecturally optimized scaffold for tendon and ligament regeneration," Biomaterials, vol. 28, No. 29, pp. 4321-4329, Oct. 2007.

Wright, E.J., Iselin, C.E, Carr, L.K. and Webster, G.D., "Pubovaginal sling using cadaveric allograft fascia for the treatment of intrinsic sphincter deficiency," J. Urol., vol. 160, No. 3, Part 1, pp. 759-762, Sep. 1998.

Zielaskowski, L.A. and Pontious, J., "Extensor hallucis longus tendon rupture repair using a fascia lata allograft," J. Am. Podiatr. Med. Assoc., vol. 92, No. 8, pp. 467-470, Sep. 2002.

Office action issued Apr. 14, 2011 in U.S. Appl. No. 12/283,661.

International Search Report and Written Opinion from corresponding PCT application PCT/US09/34071, dated Aug. 25, 2009.

Office action issued Aug. 13, 2010 in Canadian Patent Application No. 2,512,730.

English translation of Office action issued Aug. 4, 2009 in Japanese Patent Application Serial No. 2006-500869.

Accousti, K.J. and Flatow, E.L., "Technical pearls on how to maximize healing of the rotator cuff," Instr Course Lect 56, pp. 3-12, 2007.

Adams, J.E., Zobitz, M.E., Reach, Jr, J.S., An, K.-N. and Steinmann, S.P., "Rotator cuff repair using an acellular dermal matrix graft: An in vivo study in a canine model," Arthroscopy 22(7), pp. 700-709, Jul. 2006.

Anderst, W.J., Les, C. and Tashman, S., "In vivo serial joint space measurements during dynamic loading in a canine model of osteoarthritis," Osteoarthritis and Cartilage 13(9), pp. 808-816, 2005.

Androjna, C., Spragg, R.K. and Derwin, K.A., "Mechanical conditioning of cell-seeded small intestine submucosa: A potential tissue-engineering strategy for tendon repair," Tissue Eng 13(2), pp. 233-243, 2007.

Aoki, M., Miyamoto, S., Okamura, K., Yamashita, T., Ikada, Y. and Matsuda, S., "Tensile properties and biological response of poly(L-lactic acid) felt graft: An experimental trial for rotator-cuff reconstruction," J Biomed Mater Res Part B: Appl Biomater 71B, pp. 252-259, 2004.

ASTM E177-90a (1996), "Standard practice for use of the terms precision and bias in ASTM test methods," pp. 1-12.

Badylak, S., Kokini, K., Tullius, B., Simmons-Byrd, A. and Morff, R., "Morphologic study of small intestinal submucosa as a body wall repair device," J Surg Res 103(2), pp. 190-202, Apr. 2002.

Baker, A.R., Abreu, E.L., Mascha, E. and Derwin, K.A., "Homotypic variation of canine flexor tendons: Implications for the design of experimental studies in animal models," J Biomech 37, pp. 959-968, 2004.

Baker, B.M., Gee, A.O., Metter, R.B., Nathan, A.S., Marklein, R.A., Burdick, J.A. and Mauck, R.L., "The potential to improve cell infiltration in composite fiber-aligned electrospun scaffolds by the selective removal of sacrificial fibers," Biomaterials 29, pp. 2348-2358, 2008.

Barber, F.A., Herbert, M.A. and Coons, D.A., "Tendon augmentation grafts: Biomechanical failure loads and failure patterns," Arthroscopy 22(5), pp. 534-538, May 2006.

Bartolozzi, A., Andreychik, D. and Ahmad, S., "Determinants of outcome in the treatment of rotator cuff disease," Clin Orthop Rel Res 308, pp. 90-97, Nov. 1994.

Barton, E.R., Gimbel, J.A., Williams, G.R. and Soslowsky, L.J., "Rat supraspinatus muscle atrophy after tendon detachment," J Orthop Res 23, pp. 259-265, 2005.

Bey, M.J., Song, H.K., Wehrli, F.W. and Soslowsky, L.J., "A noncontact, nondestructive method for quantifying intratissue deformations and strains," J Biomech Engin 124, pp. 253-258, Apr. 2002.

Bishop, J., Klepps, S., Lo, I.K., Bird, J., Gladstone, J.N. and Flatow, E.L., "Cuff integrity after arthroscopic versus open rotator cuff repair: A prospective study," J Shoulder Elbow Surg 15(3), pp. 290-299, May/Jun. 2006.

Boileau, P., Brassart, N., Watkinson, D.J., Carles, M., Hatzidakis, A.M. and Krishnan, S.G., "Arthroscopic repair of full-thickness tears of the supraspinatus: Does the tendon really heal?" J Bone Joint Surg 87-A(6), pp. 1229-1240, Jun. 2005.

Bullard, K.M., Longaker, M.T. and Lorenz, H.P., "Fetal wound healing: Current biology," World J Surg 27(1), pp. 54-61, Jan. 2003.

Burkhart, S.S., "Partial repair of massive rotator cuff tears: The evolution of a concept," Orthop Clin North Am 28(1), pp. 125-132, Jan. 1997.

Burkhart, S.S., Diaz Pagan, J.L., Wirth, M.A. and Athanasiou, K.A., "Cyclic loading of anchor-based rotator cuff repairs: Confirmation of the tension overload phenomenon and comparison of suture anchor fixation with transosseous fixation," Arthroscopy 13(6), pp. 720-724, Dec. 1997.

Cantor, J.O. and Nadkarni, P.P., "Hyaluronan: The Jekyll and Hyde molecule," Inflammation & Allergy—Drug Targets 5(4), pp. 257-260, 2006.

Carpenter, J.E., Flanagan, C.L., Thomopoulos, S., Yian, E.H. and Soslowsky, L.J., "The effects of overuse combined with intrinsic or extrinsic alterations in an animal model of rotator cuff tendinosis," Am J Sports Med 26(6), pp. 801-807, 1998.

Carpenter, J.E., Thomopoulos, S., Flanagan, C.L., DeBano, C.M. and Soslowsky, L.J., "Rotator cuff defect healing: A biomechanical and histologic analysis in an animal model," J Shoulder Elbow Surg 7(6), pp. 599-605, Nov./Dec. 1998.

Carpenter, J.E., Thomopoulos, S. and Soslowsky, L.J., "Animal models of tendon and ligament injuries for tissue engineering applications," Clin Orthop Relat Res 367S, pp. S296-8311, Oct. 1999.

Chen, G.-Q. and Wu, Q., "The application of polyhydroxyalkanoates as tissue engineering materials," Biomaterials 26, pp. 6565-6578, 2005.

Claerhout, F., Verbist, G., Verbeken, E., Konstantinovic, M., De Ridder, D. and Deprest, J., "Fate of collagen-based implants used in pelvic floor surgery: A 2-year follow-up study in a rabbit model," Am J Obstet Gynecol 198, pp. 94.e1-94.e6, Jan. 2008.

Cofield, R.H., Parvizi, J., Hoffmeyer, P.J., Lanzer, W.L., Ilstrup, D.M. and Rowland, C.H., "Surgical repair of chronic rotator cuff tears: A prospective long-term study," J Bone Joint Surg 83-A(1), pp. 71-77, Jan. 2001.

Cole, B.J., Gomoll, A.H., Yanke, A., Pylawka, T., Lewis, P., MacGillivray, J.D. and Williams, J.M., "Biocompatibility of a polymer patch for rotator cuff repair," Knee Surg Sports Traumatol Arthrosc 15, pp. 632-637, 2007.

Coleman, S.H., Fealy, S., Ehteshami, J.R., MacGillivray, J.D., Altchek, D.W., Warren, R.F. and Turner, S., "Chronic rotator cuff injury and repair model in sheep," J Bone Joint Surg 85-A(12), pp. 2391-2402, Dec. 2003.

Cook, J.L., Fox, D.B., Kuroki, K., Jayo, M. and De Deyne, P.G., "In vitro and in vivo comparison of five biomaterials used for orthopedic soft tissue augmentation," Am J Vet Res 69(1), pp. 148-156, Jan. 2008.

Costa-Pinto, A.R., Salgado, A.J., Correlo, V.M., Sol, P., Bhattacharya, M., Charbord, P., Reis, R.L. and Neves, N.M., "Adhesion, proliferation and osteogenic differentiation of a mouse mesenchymal stem cell line (BMC9) seeded on novel melt-based chitosan/polyester 3D porous scaffolds," Tissue Eng Part A 14(6) pp. 1049-1057, 2008.

Cummins, C.A. and Murrell, G.A.C., "Mode of failure for rotator cuff repair with suture anchors identified at revision surgery," J Shoulder Elbow Surg 12(2), pp. 128-133, Mar./Apr. 2003.

Cuttle, L., Nataatmadja, M., Fraser, J.F., Kempf, M., Kimble, R.M. and Hayes, M.T., "Collagen in the scarless fetal skin wound: Detection with Picrosirius-polarization," Wound Rep Reg 13(2), pp. 198-204, 2005.

Dejardin, L.M., Arnoczky, S.P., Ewers, B.J., Haut, R.C. and Clarke, R.B., "Tissue-engineered rotator cuff tendon using porcine small intestine submucosa: Histologic and mechanical evaluation in dogs," Am J Sports Med 29(2), pp. 175-184, 2001.

Derwin, K., Androjna, C., Spencer, E., Safran, O., Bauer, T.W., Hunt, T., Caplan, A. and Iannotti, J., "Porcine small intestine submucosa as a flexor tendon graft," Clin Orthop Relat Res 423, pp. 245-252, Jun. 2004.

Derwin, K.A., Baker, A.R., Codsi, M.J. and Iannotti, J.P., "Assessment of the canine model of rotator cuff injury and repair," J Shoulder Elbow Surg 16(5S), pp. 140S-148S, Sep./Oct. 2007.

Derwin, K.A., Baker, A.R., Spragg, R.K., Leigh, D.R. and Iannotti, J.P., "Commercial extracellular matrix scaffolds for rotator cuff tendon repair: Biomechanical, biochermical, and cellular properties," J Bone Joint Surg 88-A(12), pp. 2665-2672, Dec. 2006.

Dines, D.M., Moynihan, D.P., Dines, J.S. and McCann, P., "Irreparable rotator cuff tears: What to do and when to do it; the surgeon's dilemma," Instr Course Lect 56, pp. 13-22, 2007.

Ellis, I., Banyard, J. and Schor, S.L., "Differential response of fetal and adult fibroblasts to cytokines: Cell migration and hyaluronan synthesis," Development 124, pp. 1593-1600, 1997.

Fabis, J., Danilewicz, M. and Omulecka, A., "Rabbit supraspinatus tendon detachment: Effects of size and time after tenotomy on morphometric changes in the muscle," Acta Orthop Scand 72(3), pp. 282-286, 2001.

Fealy, S., Rodea, S.A., MacGillivray, J.D., Nixon, A.J., Adler, R.S. and Warren, R.F., "Biomechanical evaluation of the relation between number of suture anchors and strength of the bone-tendon interface in a goat rotator cuff model," Arthroscopy 22(6), pp. 595-602, Jun. 2006.

Fini, M., Torricelli, P., Giavaresi, G., Rotini, R., Castagna, A. and Giardino, R., "In vitro study comparing two collageneous membranes in view of their clinical application for rotator cuff tendon regeneration," J Orthop Res 25, pp. 98-107, Jan. 2007.

Funakoshi, T., Majima, T., Suenaga, N., Iwasaki, N., Yamane, S. and Minami, A., "Rotator cuff regeneration using chitin fabric as an acellular matrix," J Shoulder Elbow Surg 15(1), pp. 112-118, Jan./Feb. 2006.

Galatz, L.M., Ball, C.M., Teefey, S.A., Middleton, W.D. and Yamaguchi, K., "The outcome and repair integrity of completely arthroscopically repaired large and massive rotator cuff tears," J Bone Joint Surg 86-A(2), pp. 219-224, Feb. 2004.

Galatz, L.M., Sandell, L.J., Rothermich, S.Y., Das, R., Mastny, A., Havlioglu, N., Silva, M.J. and Thomopoulos, S., "Characteristics of the rat supraspinatus tendon during tendon-to-bone healing after acute injury," J Orthop Res 24, pp. 541-550, Mar. 2006.

Gazielly, D.F., Gleyze, P. and Montagnon, C., "Functional and anatomical results after rotator cuff repair," Clin Orthop Rel Res 304, pp. 43-53, Jul. 1994.

Gerber, C., Fuchs, B. and Hodler, J., "The results of repair of massive tears of the rotator cuff," J Bone Joint Surg 82-A(4), pp. 505-515, Apr. 2000.

Gerber, C., Meyer, D.C., Schneeberger, A.G., Hoppeler, H. and Von Rechenberg, B., "Effect of tendon release and delayed repair on the structure of the muscles of the rotator cuff: An experimental study in sheep," J Bone Joint Surg 86-A(9), pp. 1973-1982, Sep. 2004.

Gerber, C., Schneeberger, A.G., Perren, S.M. and Nyffeler, R.W., "Experimental rotator cuff repair: A preliminary study," J Bone Joint Surg 81-A(9), pp. 1281-1290, Sep. 1999.

Gimbel, J.A., Van Kleunen, J.P., Mehta, S., Perry, S.M., Williams, G.R. and Soslowsky, L.J., "Supraspinatus tendon organizational and mechanical properties in a chronic rotator cuff tear animal model," J Biomech 37, pp. 739-749, 2004.

Goldberg, V.M. and Buckwalter, J.A., "Hyaluronans in the treatment of osteoarthritis of the knee: Evidence for disease-modifying activity," Osteoarthritis and Cartilage 13(3), pp. 216-224, 2005.

Goutallier, D., Postel, J.-M., Gleyze, P., Leguilloux, P. and Van Driessche, S., "Influence of cuff muscle fatty degeneration on anatomic and functional outcomes after simple suture of full-thickness tears," J Shoulder Elbow Surg 12(6), pp. 550-554, Nov./Dec. 2003.

Hamada, K., Tomonaga, A., Gotoh, M., Yamakawa, H. and Fukuda, H., "Intrinsic healing capacity and tearing process of torn supraspinatus tendons: In situ hybridization study of α1(I) procollagen mRNA," J Orthop Res 15(1), pp. 24-32, 1997.

Handa, V.L., Jensen, J.K., Germain, M.M. and Ostergard, D.R., "Banked human fascia lata for the suburethral sling procedure: A preliminary report," Obstet Gynecol 88(6), pp. 1045-1049, Dec. 1996.

Harryman, D.T., Mack, L.A., Wang, K.Y., Jackins, S.E., Richardson, M.L. and Matsen, F.A., "Repairs of the rotator cuff: Correlation of functional results with integrity of the cuff," J Bone Joint Surg 73-A(7), pp. 982-989, Aug. 1991.

Hawkins, R.H. and Dunlop, R., "Nonoperative treatment of rotator cuff tears," Clin Orthop Relat Res 321, pp. 178-188, Dec. 1995.

Heikel, H.V.A., "Rupture of the rotator cuff of the shoulder: Experiences of surgical treatment," Acta Orthop Scand 39(4), pp. 477-492, 1968.

Iannotti, J.P., "Full thickness rotator cuff tears: Factors affecting surgical outcome," J Am Acad Orthop Surg 2(2), pp. 87-95, Mar./Apr. 1994.

Inoue, N., Ikeda, K., Aro, H.T., Frassica, F.J., Sim, F.H. and Chao, E.Y.S., "Biologic tendon fixation to metallic implant augmented with autogenous cancellous bone graft and bone marrow in a canine model," J Orthop Res 20, pp. 957-966, 2002.

Kambic, H.E. and McDevitt, C.A., "Spatial organization of types I and II collagen in the canine meniscus," J Orthop Res 23, pp. 142-149, 2005.

Kidd, K.R., Dal Ponte, D.B., Kellar, R.S. and Williams, S.K., "A comparative evaluation of the tissue responses associated with polymeric implants in the rat and mouse," J Biomed Mater Res 59, pp. 682-689, 2002.

Kimura, A., Aoki, M., Fukushima, S., Ishii, S. and Yamakoshi, K., "Reconstruction of a defect of the rotator cuff with polytetrafluoroethylene felt graft: Recovery of tensile strength and histocompatibility in an animal model," J Bone Joint Surg (Br) 85-B(2), pp. 282-287, Mar. 2003.

Kobayashi, M., Itoi, E., Minagawa, H., Miyakoshi, N., Takahashi, S., Tuoheti, Y., Okada, K. and Shimada, Y., "Expression of growth factors in the early phase of supraspinatus tendon healing in rabbits," J Shoulder Elbow Surg 15(3), pp. 371-377, May/Jun. 2006.

Koh, J.L., Szomor, Z., Murrell, G.A.C. and Warren, R.F., "Supplementation of rotator cuff repair with a bioresorbable scaffold," Am J Sports Med 30(3), pp. 410-413, 2002.

Koike, Y., Trudel, G., Curran, D. and Uhthoff, H.K., "Delay of supraspinatus repair by up to 12 weeks does not impair enthesis formation: A quantitative histologic study in rabbits," J Orthop Res 24, pp. 202-210, Feb. 2006.

Koike, Y., Trudel, G. and Uhthoff, H.K., "Formation of a new enthesis after attachment of the supraspinatus tendon: A quantitative histologic study in rabbits," J Orthop Res 23, pp. 1433-1440, 2005.

Konstantinovic, M.L., Lagae, P., Zheng, F., Verbeken, E.K., De Ridder, D. and Deprest, J.A., Comparison of host response to polypropylene and non-cross-linked porcine small intestine serosal-derived collagen impants in a rat model, BJOG 112, pp. 1554-1560, Nov. 2005.

Kuhlmann, J.N., Luboinski, J., Mimoun, M., Orcel, L. and Baux, S., "Reconstruction of the medial collateral ligament of the knee in rats, using a free autogenous transplant of fascia lata, ligament or tendon," Acta Orthop Belg 60(1), pp. 10-18, 1994.

Laschke, M.W., Haufel, J.M., Thorlacius, H. and Menger, M.D., "New experimental approach to study host tissue response to surgical mesh materials in vivo," J Biomed Mater Res 74A, pp. 696-704, 2005.

Lemer, M.L., Chaikin, D.C. and Blaivas, J.G., "Tissue strength analysis of autologous and cadaveric allografts for the pubovaginal sling," Neurourol Urodyn 18, pp. 497-503, 1999.

Lin, J., Lindsey, M.L., Zhu, B., Agrawal, C.M. and Bailey, S.R., "Effects of surface-modified scaffolds on the growth and differentiation of mouse adipose-derived stromal cells," J Tissue Eng Regen Med 1, pp. 211-217, 2007.

Lin, J.S.N., Tsai, Y.-S., Lin, Y.-M., Lin, C.-S. and Chow, N.-H., "Age-associated changes in collagen content and its subtypes within rat corpora cavernosa with computerized histomorphometric analysis," Urology 57(4), pp. 837-842, 2001.

Lindberg, K. and Badylak, S.F., "Porcine small intestinal submucosa (SIS): A bioscaffold supporting in vitro primary human epidermal cell differentiation and synthesis of basement membrane proteins," Burns 27, pp. 254-266, 2001.

Lindman, J.P., Talbert, M., Zhang, W., Powell, B., Accortt, N.A. and Rosenthal, E.L., "Promotion of acellular dermal matrix resolution in vitro by matrix metalloproteinase-2," Arch Facial Plast Surg 8, pp. 208-212, May/Jun. 2006.

Longo, U.G., Franceschi, F., Ruzzini, L., Rabitti, C., Morini, S., Maffulli, N., Forriol, F. and Denaro V., "Light microscopic histology of supraspinatus tendon ruptures," Knee Surg Sports Traumatol Arthrosc 15, pp. 1390-1394, 2007.

Lorenz, H.P., Whitby, D.J., Longaker, M.T. and Adzick, N.S., "Fetal wound healing: The ontogeny of scar formation in the non-human primate," Ann Surg 217(4), pp. 391-396, Apr. 1993.

MacGillivray, J.D., Fealy, S., Terry, M.A., Koh, J.L., Nixon, A.J. and Warren, R.F., "Biomechanical evaluation of a rotator cuff defect model augmented with a bioresorbable scaffold in goats," J Shoulder Elbow Surg 15(5), pp. 639-644, Sep./Oct. 2006.

Malcarney, H.L., Bonar, F. and Murrell, G.A.C., "Early inflammatory reaction after rotator cuff repair with a porcine small intestine submucosal implant: A report of 4 cases," Am J Sports Med 33(6), pp. 907-911, 2005.

Marsolais, D., Cote, C.H. and Frenette, J., "Neutrophils and macrophages accumulate sequentially following Achilles tendon injury," J Orthop Res 19, pp. 1203-1209, 2001.

Matsumoto, F., Uhthoff, H.K., Trudel, G. and Loehr, J.F., "Delayed tendon reattachment does not reverse atrophy and fat accumulation of the supraspinatus—an experimental study in rabbits," J Orthop Res 20, pp. 357-363, 2002.

Meinel, L., Hofmann, S., Karageorgiou, V., Kirker-Head, C., McCool, J., Gronowicz, G., Zichner, L., Langer, R., Vunjak-Novakovic, G. and Kaplan, D.L., "The inflammatory responses to silk films in vitro and in vivo," Biomaterials 26, pp. 147-155, 2005.

Melillo, A.S., Savoie III, F.H. and Field, L.D., "Massive rotator cuff tears: Debridement versus repair," Orthop Clin North Am 28(1), pp. 117-124, Jan. 1997.

Metcalf, M.H., Savoie III, F.H. and Kellum, B., "Surgical technique for xenograft (SIS) augmentation of rotator-cuff repairs," Operative Techniques Orthop 12(3), pp. 204-208, Jul. 2002.

Meyer, D.C., Hoppeler, H., Von Rechenberg, B. and Gerber, C., "A pathomechanical concept explains muscle loss and fatty muscular changes following surgical tendon release," J Orthop Res 22, pp. 1004-1007, 2004.

Meyer, D.C., Lajtai, G., Von Rechenberg, B., Pfirrmann, C.W.A. and Gerber, C., "Tendon retracts more than muscle in experimental chronic tears of the rotator cuff," J Bone Joint Surg (Br) 88-B(11), pp. 1533-1538, Nov. 2006.

Nair, M.B., Bernhardt, A., Lode, A., Heinemann, C., Thieme, S., Hanke, T., Varma, H., Gelinsky, M. and John, A., "A bioactive triphasic ceramic-coated hydroxyapatite promotes proliferation and osteogenic differentiation of human bone marrow stromal cells," J Biomed Mater Res 90A, pp. 533-542, 2009.

Nakamura, K., Yokohama, S., Yoneda, M., Okamoto, S., Tamaki, Y., Ito, T., Okada, M., Aso, K. and Makino, I., "High, but not low, molecular weight hyaluronan prevents T-cell mediated liver injury by reducing proinflammatory cytokines in mice," J Gastroenterol 39, pp. 346-354, 2004.

Noble, P.W., "Hyaluronan and its catabolic products in tissue injury and repair," Matrix Biol 21, pp. 25-29, 2002.

Noerdlinger, M.A., Cole, B.J., Stewart, M. and Post, M., "Results of pectoralis major transfer with fascia lata autograft augmentation for scapula winging," J Shoulder Elbow Surg 11(4), pp. 345-350, Jul./Aug. 2002.

Oguma, H., Murakami, G., Takahashi-Iwanaga, H., Aoki, M. and Ishii, S., "Early anchoring collagen fibers at the bone-tendon interface are conducted by woven bone formation: Light microscope and scanning electron microscope observation using a canine model," J Orthop Res 19, pp. 873-880, 2001.

Patil, S.D., Papadmitrakopoulos, F. and Burgess, D.J., "Concurrent delivery of dexamethasone and VEGF for localized inflammation control and angiogenesis," J Control Release 117, pp. 68-79, 2007.

Pearsall IV, A.W., Madanagopal, S.G. and Karas, S.G., "Transfer of the latissimus dorsi as a salvage procedure for failed debridement and attempted repair of massive rotator cuff tears," Orthopedics 30(11), pp. 943-949, Nov. 2007.
Prestwich, G.D., "Simplifying the extracellular matrix for 3-D cell culture and tissue engineering: A pragmatic approach," J. Cell Biochem 101, pp. 1370-1383, 2007.
Riley, G.P., Harrall, R.L., Constant, C.R., Chard, M.D., Cawston, T.E. and Hazleman, B.L., "Tendon degeneration and chronic shoulder pain: Changes in the collagen composition of the human rotator cuff tendons in rotator cuff tendinitis," Ann Rheum Dis 53, pp. 359-366, 1994.
Rockwood, C.A., Williams, G.R. and Burkhead, W.Z., "Debridement of degenerative, irreparable lesions of the rotator cuff," J Bone Joint Surg 77-A(6), pp. 857-866, Jun. 1995.
Rodeo, S.A., Potter, H.G., Kawamura, S., Turner, A.S., Kim, H.J. and Atkinson, B.L., "Biologic augmentation of rotator cuff tendon-healing with use of a mixture of osteoinductive growth factors," J Bone Joint Surg 89-A(11), pp. 2485-2497, Nov. 2007.
Romeo, A.A., Hang, D.W., Bach, Jr., B.R. and Shott, S., "Repair of full thickness rotator cuff tears: Gender, age, and other factors affecting outcome," Clin Orthop Rel Res 367, pp. 243-255, Sep. 1999.
Safran, O., Derwin, K.A., Powell, K. and Iannotti, J.P., "Changes in rotator cuff muscle volume, fat content, and passive mechanics after chronic detachment in a canine model," J Bone Joint Surg 87-A(12), pp. 2662-2670, Dec. 2005.
Sano, H., Kumagai, J. and Sawai, T., "Experimental fascial autografting for the supraspinatus tendon defect: Remodeling process of the grafted fascia and the insertion into bone," J Shoulder Elbow Surg 11(2), pp. 166-173, Mar./Apr. 2002.
Schlegel, T.F., Hawkins, R.J., Lewis, C.W., Motta, T. and Turner, A.S., "The effects of augmentation with swine small intestine submucosa on tendon healing under tension: Histologic and mechanical evaluations in sheep," Am J Sports Med 34(2), pp. 275-280, 2006.
Schlegel, T.F., Hawkins, R.J., Lewis, C.W. and Turner, A.S., "An in vivo comparison of the modified Mason-Allen suture technique versus an inclined horizontal mattress suture technique with regard to tendon-to-bone healing: A biomechanical and histologic study in sheep," J Shoulder Elbow Surg 16(1), pp. 115-121, Jan./Feb. 2007.
Sclamberg, S.G., Tibone, J.E., Itamura, J.M. and Kasraeian, S., "Six-month magnetic resonance imaging follow-up of large and massive rotator cuff repairs reinforced with porcine small intestinal submucosa," J Shoulder Elbow Surg 13(5), pp. 538-541, Sep./Oct. 2004.
Seiler, J.G., Gelberman, R.H., Williams, C.S., Woo, S.L.-Y., Dickersin, G.R., Sofranko, R., Chu, C.R. and Rosenberg, A.E., "Autogenous flexor-tendon grafts: A biomechanical and morphological study in dogs," J Bone Joint Surg 75-A(7), pp. 1004-1014, Jul. 1993.
Setton, L.A., Mow, V.C., Muller, F.J., Pita, J.C. and Howell, D.S., "Mechanical behavior and biochemical composition of canine knee cartilage following periods of joint disuse and disuse with remobilization," Osteoarthritis and Cartilage 5(1), pp. 1-16, 1997.
Shen, Y.H., Shoichet, M.S. and Radisic, M., "Vascular endothelial growth factor immobilized in collagen scaffold promotes penetration and proliferation of endothelial cells," Acta Biomater 4, pp. 477-489, 2008.
Soler, J.A., Gidwani, S. and Curtis, M.J., "Early complications from the use of porcine dermal collagen implants (Permacol) as bridging constructs in the repair of massive rotator cuff tears: A report of 4 cases," Acta Orthop Belg 73(4), pp. 432-436, 2007.
Soslowsky, L.J., Carpenter, J.E., Debano, C.M., Banerji, I. and Moalli, M.R., "Development and use of an animal model for investigations on rotator cuff disease," J Shoulder Elbow Surg 5(5), pp. 383-392, Sep./Oct. 1996.
Soslowsky, L.J., Thomopoulos, S., Esmail, A., Flanagan, C.L., Iannotti, J.P., Williamson III, J.D. and Carpenter, J.E., "Rotator cuff tendinosis in an animal model: Role of extrinsic and overuse factors," Ann Biomed Eng 30, pp. 1057-1063, 2002.
Soslowsky, L.J., Thomopoulos, S., Tun, S., Flanagan, C.L., Keefer, C.C., Mastaw, J. and Carpenter, J.E., "Neer Award 1999. Overuse activity injures the supraspinatus tendon in an animal model: A histologic and biomechanical study," J Shoulder Elbow Surg 9(2), pp. 79-84, Mar./Apr. 2000.
St. Pierre, P., Olson, E.J., Elliott, J.J., O'Hair, K.C., McKinney, L.A. and Ryan, J., "Tendon-healing to cortical bone compared with healing to a cancellous trough: A biomechanical and histological evaluation in goats," J Bone Joint Surg 77-A(12), pp. 1858-1866, Dec. 1995.
Tammi, M.I., Day, A.J. and Turley, E.A., "Hyaluronan and homeostasis: A balancing act," J Biol Chem 277(7), pp. 4581-4584, Feb. 15, 2002.
Thimm, B.W., Unger, R.E., Neumann, H.-G. and Kirkpatrick, C.J., "Biocompatibility studies of endothelial cells on a novel calcium phosphate/SiO2-xerogel composite for bone tissue engineering," Biomed Mater 3. 015007 (10pgs), 2008.
Thomopoulos, S., Hattersley, G., Rosen, V., Mertens, M., Galatz, L., Williams, G.R. and Soslowsky, L.J., "The localized expression of extracellular matrix components in healing tendon insertion sites: An in situ hybridization study," J Orthop Res 20, pp. 454-463, 2002.
Thomopoulos, S., Soslowsky, L.J., Flanagan, C.L., Tun, S., Keefer, C.C., Mastaw, J. and Carpenter, J.E., "The effect of fibrin clot on healing rat supraspinatus tendon defects," J Shoulder Elbow Surg 11(3), pp. 239-247, May/Jun. 2002.
Thomopoulos, S., Williams, G.R. and Soslowsky, L.J., "Tendon to bone healing: Differences in biomechanical, structural, and compositional properties due to a range of activity levels," J Biomech Engin 125, pp. 106-113, Feb. 2003.
Thomsen, P., Bjursten, L.M. and Ericson, L.E., "Implants in the abdominal wall of the rat," Scand J Plast Reconstr Surg 20, pp. 173-182, 1986.
Toole, B.P. and Gross, J., "The extracellular matrix of the regenerating newt limb: Synthesis and removal of hyaluronate prior to differentiation," Dev Biol 25, pp. 57-77, 1971.
Uhthoff, H.K., Matsumoto, F., Trudel, G. and Himori, K., "Early reattachment does not reverse atrophy and fat accumulation of the supraspinatus—an experimental study in rabbits," J Orthop Res 21, pp. 386-392, 2003.
Uhthoff, H.K., Trudel, G. and Himori, K., "Relevance of pathology and basic research to the surgeon treating rotator cuff disease," J Orthop Sci 8, pp. 449-456, 2003.
Walton, J.R., Bowman, N. K., Khatib, Y., Linklater, J. and Murrell, G.A.C., "Restore orthobiologic implant: Not recommended for augmentation of rotator cuff repairs," J Bone Joint Surg 89-A(4), pp. 786-791, Apr. 2007.
Yildirim, A., Basok, E.K., Gulpinar, T., Gurbuz, C., Zemheri, E. and Tokuc, R., "Tissue reactions of 5 sling materials and tissue material detachment strength of 4 synthetic mesh materials in a rabbit model," J Urol 174, pp. 2037-2040, Nov. 2005.
Zalavras, C.G., Gardocki, R., Huang, E., Stevanovic, M., Hedman, T. and Tibone, J., "Reconstruction of large rotator cuff tendon defects with porcine small intestinal submucosa in an animal model," J Shoulder Elbow Surg 15(2), pp. 224-231, Mar./Apr. 2006.
Zheng, F., Lin, Y., Verbeken, E., Claerhout, F., Fastrez, M., De Ridder, D. and Deprest, J., "Host response after reconstruction of abdominal wall defects with porcine dermal collagen in a rat model," Am J Obstet Gynecol 191, pp. 1961-1970, 2004.
Zheng, M.H., Chen, J., Kirilak, Y., Willers, C., Xu, J. and Wood, D., "Porcine small intestine submucosa (SIS) is not an acellular collagenous matrix and contains porcine DNA: Possible implications in human implantation," J Biomed Mater Res Part B: Appl Biomater 73B, pp. 61-67, 2005.
Aoki, M., Oguma, H., Fukushima, S., Ishii, S., Ohtani, S. and Murakami, G., "Fibrous connection to bone after immediate repair of the canine infraspinatus: The most effective bony surface for tendon attachment," J Shoulder Elbow Surg 10(2), pp. 123-128, Mar./Apr. 2001.
Gimbel, J.A., Mehta, S., Van Kleunen, J.P., Williams, G.R. and Soslowsky, L.J., "The tension required at repair to reappose the supraspinatus tendon to bone rapidly increases after injury," Clin Orthop Rel Res 426, pp. 258-265, Sep. 2004.
Yang, S.H., Chen, P.Q., Chen, Y.F. and Lin, F.H., "An In-vitro Study on Regeneration of Human Nucleus Pulposus by Using Gelatin/Chondroitin-6-Sulfate/Hyaluronan Tri-copolymer Scaffold," Artificial Organs, vol. 29, No. 10, pp. 806-814, 2005.

FIG. 5

MOLECULAR ENHANCEMENT OF EXTRACELLULAR MATRIX AND METHODS OF USE

CROSS-REFERENCE TO RELATED APPLICATIONS

This application claims the benefit of U.S. Provisional Application No. 61/065,527 filed Feb. 13, 2008, the entire disclosure of which is incorporated herein by reference.

BACKGROUND OF THE INVENTION

The rotator cuff comprises four muscles that control shoulder movement and their associated tendons by which the muscles are attached to the humeral head (the end of the humerus that forms part of the shoulder joint). Together with the joint capsule, these muscles and tendons form a cuff that surrounds the head of the humerus. The tendons are thick, ribbon-like structures having high tensile strength. They not only hold the shoulder muscles and the humerus together, but also transmit forces exerted by those muscles to induce corresponding movement of the humerus. In a healthy subject, the tendons are fully attached at one end to, and envelop, a portion of the humeral-head surface. When a rotator cuff tear occurs, the joint capsule and one or more of the tendons become(s) partially or entirely torn away from the humeral head, creating both a painful and a functionally debilitating condition.

Current treatment for rotator-cuff tears is to suture the torn tendon back to the bone of the humeral head. The sutures hold the tendon in contact with the bone, preferably long enough for the tendon to heal to the bone and form a bridge that will re-establish the tendon-bone connection and restore normal function. The sutures that are used possess sufficient tensile strength to retain the tendon and bone together during the healing process. However, the tendon is a fibrous tissue that can be torn by the sutures. Commonly, the sutures will align with the fascicular structure of the tendon and tear right through it under sufficient tensile force, thus undoing the surgical repair before tendon-to-bone healing is complete. The sutures can also tear through the bone under sufficient force, particularly in older subjects who form the bulk of rotator-cuff-tear patients and whose bones tend to be more osteoporotic.

In fact, rotator-cuff tears affect 40% or more of those over age 60 and cost the US economy approximately $3 billion per year. The repair failure rate of large to massive rotator cuff tears ranges from 20 to 90%. High re-tear rates are a result of mechanical factors (e.g., tear size, repair technique, rehabilitation protocol) as well as biologic factors (e.g., age, tear chronicity, tendon quality, disease) that may compromise the patients' intrinsic capacity to heal. All of these factors may also contribute to the propensity of the sutures to tear through the tendon and bone before healing is complete, thus contributing to the re-tear rate. Hence, there is a need for repair strategies that provide adequate strength as well as stimulate and enhance healing potential.

BRIEF SUMMARY OF THE INVENTION

A composition is provided including a derived extracellular matrix having incorporated therein a macromolecular network of polycarboxylate or polyamine macromolecules that have been cross-linked via dihydroxyphenyl linkages. The macromolecular network is interlocked within the extracellular matrix.

A method of making an implantable composition is also provided. The method includes impregnating a derived extracellular matrix with hyaluronan macromolecules that have hydroxyphenyl side groups substituted thereon; and thereafter reacting the hydroxyphenyl side groups to form dihydroxyphenyl linkages, thereby incorporating a cross-linked macromolecular network of hyaluronan that is interlocked within the extracellular matrix.

A method of reinforcing a tissue repair, or repairing a tissue defect or gap, is also provided. The method includes providing a patch comprising a derived extracellular matrix having impregnated therein polycarboxylate or polyamine macromolecules that have hydroxyphenyl side groups substituted thereon; reacting the hydroxyphenyl side groups to form dihydroxyphenyl linkages, thereby incorporating a cross-linked macromolecular network of said polycarboxylate or polyamine macromolecules that is interlocked within the extracellular matrix; identifying an appropriate tissue defect or gap in animal or human tissue in vivo; and applying the patch to either reinforce the tissue repair or cover the tissue defect or gap.

A patch for reinforcing a tissue repair, or repairing a tissue defect or gap, is also provided. The patch includes a derived extracellular matrix having impregnated therein a macromolecular network of polycarboxylate or polyamine macromolecules that have been cross-linked via dihydroxyphenyl linkages. The macromolecular network is incorporated in and interlocked within the extracellular matrix. In preferred embodiments, the derived extracellular matrix is fascia lata and the macromolecules are hyaluronan molecules that have been substituted with tyramine and cross-linked via dityramine linkages.

BRIEF DESCRIPTION OF THE DRAWINGS

The file of this patent contains at least one drawing executed in color. Copies of this patent with color drawings will be provided by the Patent Office upon request and payment of the necessary fee.

FIG. 5 is a series of two photographs showing the distribution of HA in fascia ECM (A) treated with water and (B) treated with tyramine-substituted HA followed by cross-linking, as described in Example 1.

DETAILED DESCRIPTION OF PREFERRED EMBODIMENTS OF THE INVENTION

Figure 1:
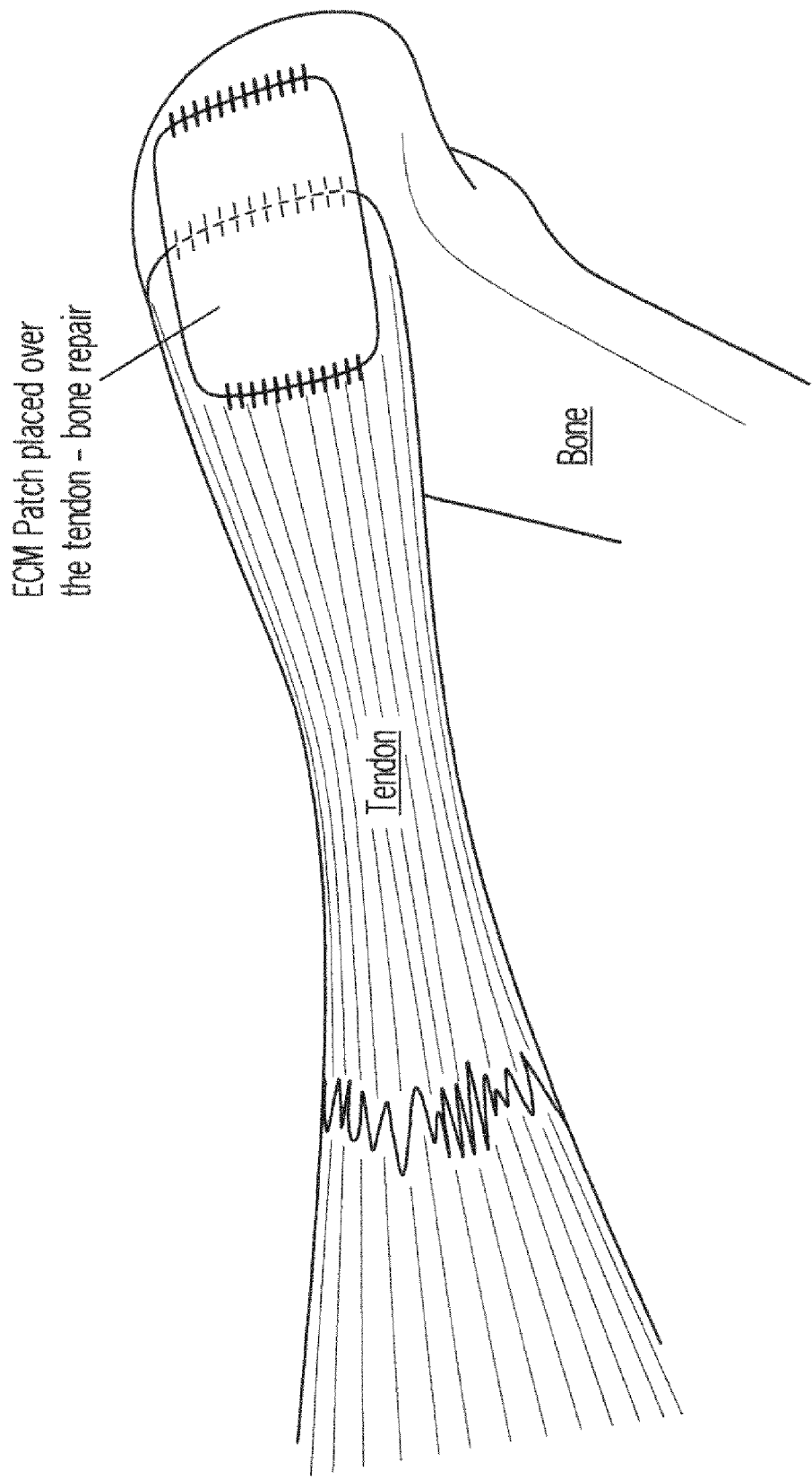
FIG. 1 is a schematic diagram of an extracellular matrix patch applied over a tendon-to-bone repair site to reinforce the repair.

Example embodiments are described below and illustrated in the drawings. These embodiments are not intended to be limitations. For example, one or more aspects can be utilized in other embodiments and even other devices or methods.

Currently, extracellular matrix ("ECM") patches are being investigated for rotator-cuff repair based on the rationale that they can provide a natural and mechanically robust scaffold that reinforces the repair, guides host cell infiltration, and fosters formation of a functional tendon-bone bridge. Extracellular matrix is the naturally-occurring extracellular part of animal or human tissue that can provide structural support to cells in addition to performing various other functions. According to preferred embodiments, patches and methods disclosed herein utilize human- or animal-derived ECM that is processed and optionally cut into a patch, and augmented ex vivo to incorporate and interlock a cross-linked macromolecular matrix to impart beneficial properties. More generally, as used herein a human- or animal-derived ECM or simply 'derived ECM' is an extracellular matrix material that is excised and harvested from an animal or human, and then processed with or without additional chemical or other treatments ex vivo to provide a patch that can be used to repair (or reinforce the repair of) a tissue defect or gap in an animal or human in need of such repair. The animal or human host who is the source of the derived ECM may or may not be the patient who is to receive the patch, made from derived ECM, to repair a tissue defect or gap.

Derived ECM may fall into two broad categories: viable derived ECM and non-viable derived ECM. Herein, viable derived ECM refers to human- or animal-derived ECM as described above, which has not been treated to remove or kill living cells present or suspended in the ECM. Accordingly, viable derived ECM will retain living cells from the host of the ECM, which were present therein upon harvesting. Viable derived ECM may be the preferred choice to prepare an autograft patch for auto-transplantation; i.e. if the tissue defect or gap in need of repair is in the host from which the ECM was derived. Alternatively, viable derived ECM also may be preferred in the case of a derived ECM host who has been tissue-typed and matched with the patient in need of the repair, to provide an allograft patch for allo-transplantation. Viable derived ECM may be derived from a living host, and used immediately (optionally even intra-operatively) to repair a tissue defect or gap, either in the ECM host or in another subject. Alternatively, the viable derived ECM may be tissue-typed and banked until needed, depending on the capability to preserve it in a viable state. In a further alternative, viable derived ECM may be derived (e.g. donated) from a recently-deceased host, wherein the cells present in the harvested ECM have not yet died.

Herein, non-viable derived ECM refers to human- or animal-derived ECM as described above, which has either been treated to remove or kill living cells present when harvested from a viable or recently deceased host, or to remove the components of necrotic cells present when harvested from cadaveric tissues after a period of time following death. Non-viable derived ECM may be the preferred option in circumstances where there is risk of inducing an unacceptable or undesirable immune response in the recipient of a patch made with the derived ECM, based on the presence of foreign living cells. Alternatively, non-viable derived ECM may be preferred when it is desirable to incorporate specific cells of known source and concentration into the patch to be formed from the derived ECM, for example autograft cells. Non-viable derived ECM also may be preferred because it is generally easier to obtain compared to viable derived ECM. In addition to obtaining non-viable ECM from cadaveric humans or animals, it may also be prepared by treating otherwise viable derived ECM with appropriate agents or techniques to kill and remove the present living cells prior to use.

The patches described herein, made from or substantially from derived ECM, are applied to repair a tissue defect or gap, or to reinforce such a repair. As used herein, a tissue defect or gap is a space between tissues of a patient (animal or human), or between adjacent portions of the same tissue, which it is desirable to join together. A tissue defect or gap can be formed from a tear or severance of tissues that once were joined, such as when a tendon tears or becomes detached from the associated bone, or when a perforation is formed (either traumatically or through a disease or other natural process) in tissue, such as an ulcer.

Herein, patches made from derived ECM and methods of using them to repair or reinforce the repair of a tissue defect or gap are disclosed. Fascia lata is one form of derived ECM useful to prepare the patches described herein. Fascia lata can be human- or animal-derived. It is particularly interesting for applications described herein, especially to reinforce tendon-to-bone repairs, because its chemical, structural and material properties are similar to tendon. Fascia lata thus has good tensile strength, an important property in retaining torn or perforated tissues together. In preferred embodiments, a patch used to reinforce or repair a tissue defect or gap is composed of, or primarily of, fascia lata. When used to repair defects in humans, the fascia lata preferably is human fascia lata, which is readily available as allograft tissue from tissue banks. Alternatively, fascia lata from other animals may be used in humans, including fascia lata derived from, e.g., pigs or cows.

FIG. 1 schematically illustrates an ECM patch, such as a fascia lata patch as preferred herein, applied and sewn over a tendon-to-bone repair site. In the illustrated embodiment, the tendon is initially repaired directly to the bone from which it has torn. This can be done by conventional techniques, as by suturing. Subsequent to this initial repair, the patch made from derived ECM is applied over the tendon-to-bone repair, and is separately attached to intact tissues located at opposite sides of the repair site. In this manner, the patch provides additional reinforcement to the repair and diminishes the tensile forces experienced by the tendon-to-bone sutures at the repair site. Thus, it will be appreciated that with the use of an appropriate ECM patch and surgical method of fixation, the sutures at the repair site (directly attached to the tendon and bone) may be less prone to tear through either the tendon or the bone. As a consequence, the tendon remains opposed to the bone in a manner that supports natural healing and the formation of a functional tendon-bone bridge. Because fascia lata ECM has mechanical properties similar to tendon, it has the inherent material properties to withstand the physiologic forces experienced during tendon-bone healing.

Figure 2:
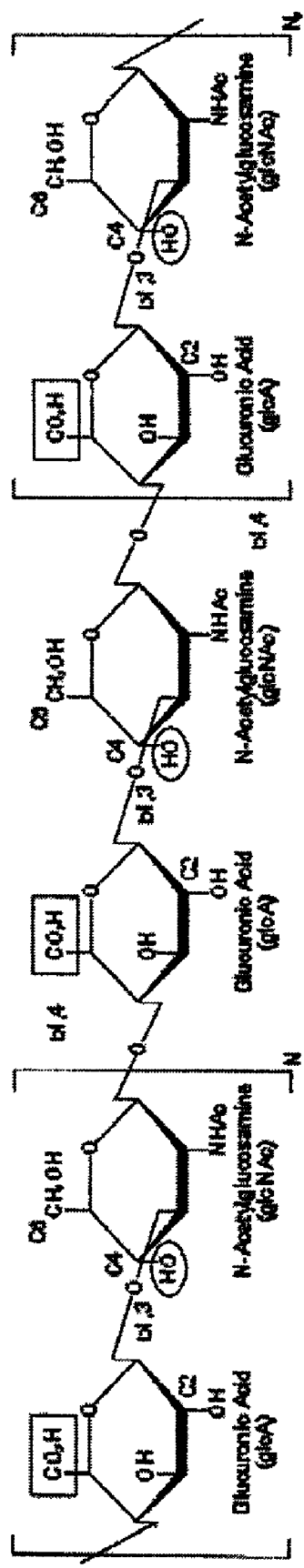
FIG. 2 is a structural formula of a hyaluronan molecule.

In addition to reinforcing the repair site, it is desirable to create and promote an environment conducive to rapid healing, which should reduce the amount of time the sutures must sustain the repair, and in turn reduce the re-tear rate. An environment that inhibits the migration of inflammatory cells and induces the migration of non-inflammatory cells would be beneficial. High molecular weight hyaluronic acid, also known as hyaluronan and abbreviated HA, the basic structure of which is shown in FIG. 2, is a ubiquitous biomolecule that is known to play a critical role in morphogenesis with myriad functions. During both morphogenesis and fetal wound healing, the persistently high levels of high molecular weight HA are thought to promote an intermediate state of cellular adhesion that allows cell shape changes and motility and/or maintenance in the undifferentiated state. Fetal wounds have abundant HA, minimal inflammation, and heal without scar formation. Based on these favorable qualities, HA has been widely investigated in tissue repair strategies. High molecular weight HA (>250 kDa) is known to possess anti-inflammatory properties leading to cell quiescence and decreased fibrosis/scar formation. High molecular weight HA may modulate inflammation by direct interaction with inflammatory cells or by creating a viscous environment that limits inflammatory cell migration and diffusion of cytokines. However, when degraded into small molecular weight fragments, HA has been shown to be pro-inflammatory and angiogenic, stimulating cell migration, cytokine production and fibrotic tissue formation. Hence in terms of therapeutic efficacy, high molecular weight HA may be beneficial as both an anti-inflammatory agent and a protective barrier against inflammatory byproducts.

Figure 3:
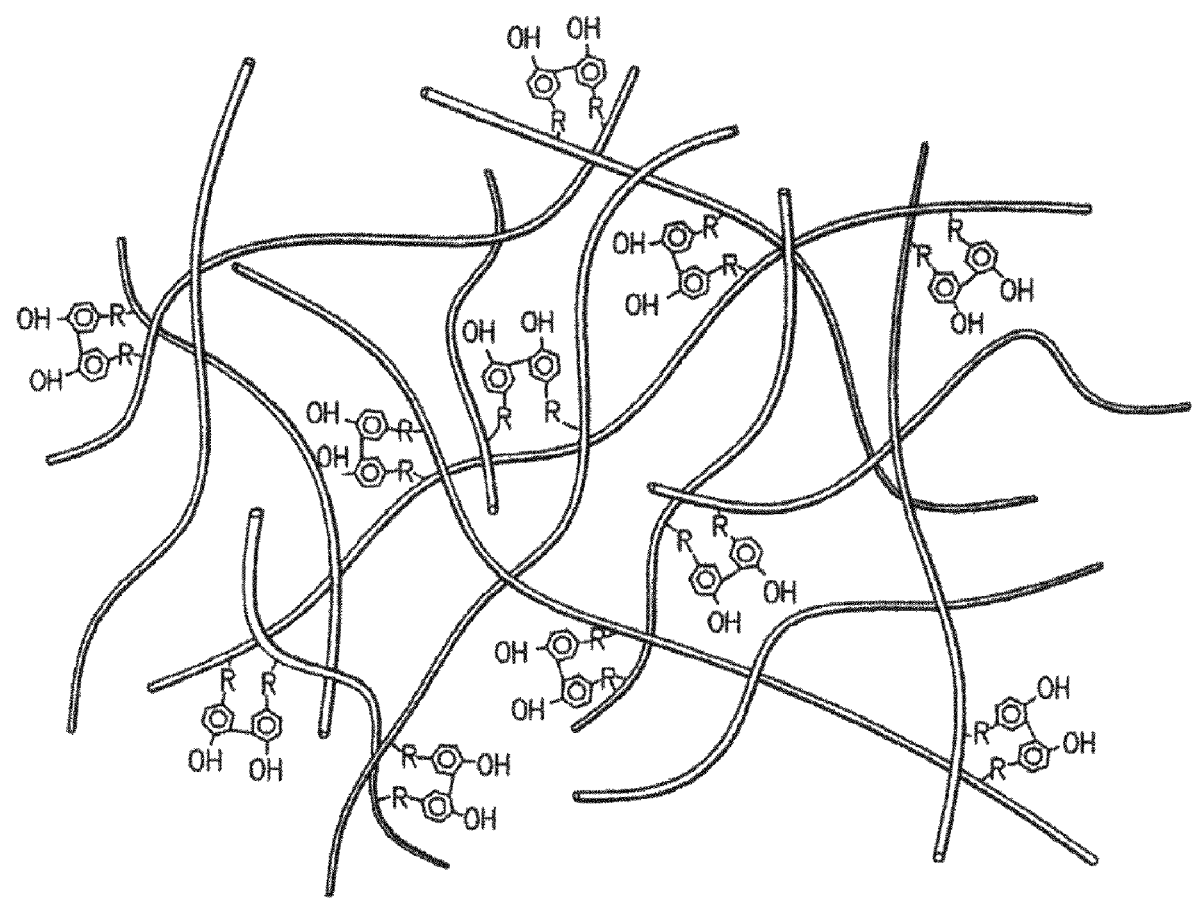
FIG. 3 is a schematic diagram of one embodiment of a dihydroxyphenyl cross-linked macromolecular network.
Figure 5:
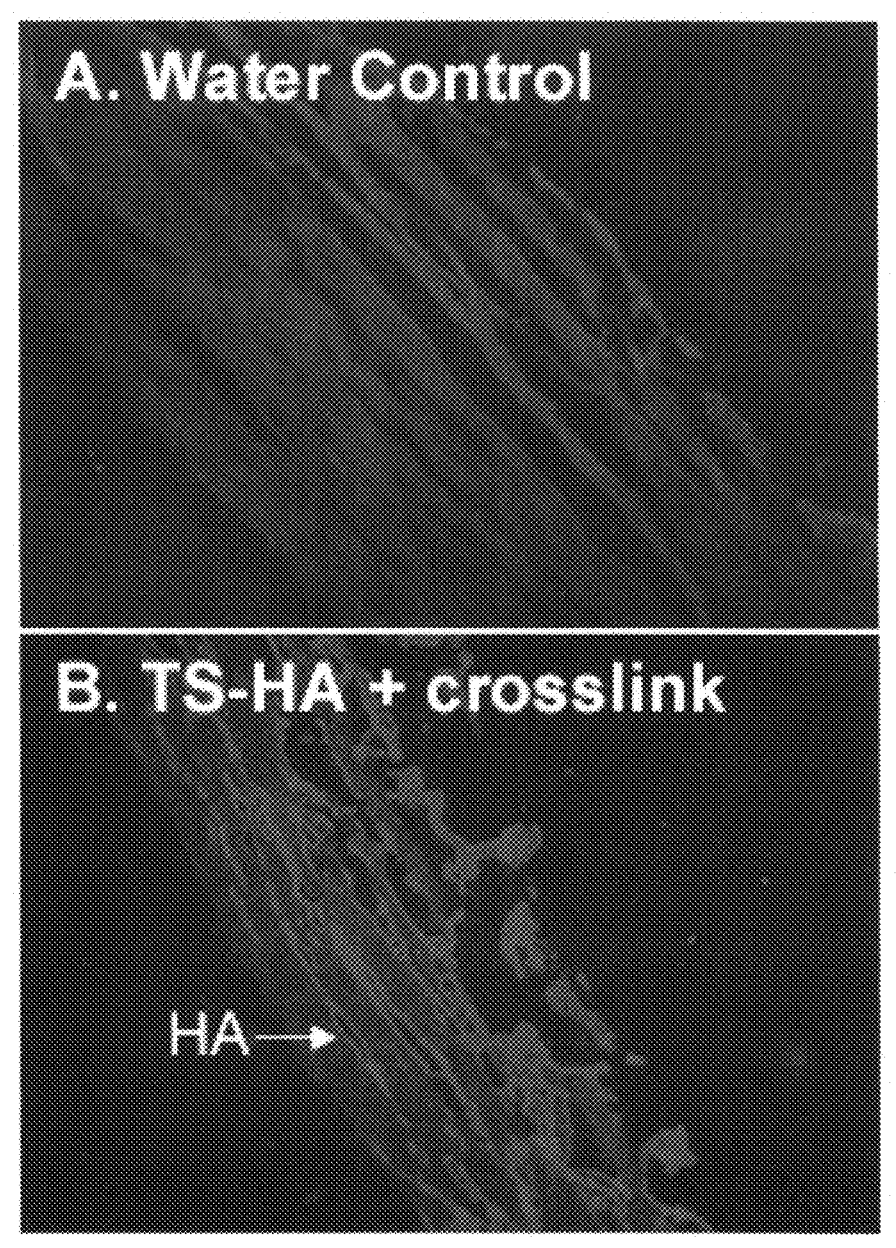

According to an embodiment, high-molecular weight HA (e.g. ~1 MDa) is incorporated into derived ECM to augment the ECM and provide an improved patch compared to using the derived ECM alone. The ECM can be any suitable derived ECM. Preferably, it is fascia lata ECM, and in the case of repairing a tissue defect in a human, preferably human fascia lata ECM. Alternatively, the derived ECM can be, e.g., fascia lata from other animals, or it can be other types of ECM, such as dermis ECM, small intestinal submucosal ECM, pericardium ECM, etc. Still further it can be a combination of derived ECM materials. In preferred embodiments, high-molecular weight HA is incorporated into the derived ECM to prepare an improved patch product. The HA is preferably hydroxyphenyl-substituted hyaluronan, more preferably tyramine-substituted hyaluronan (TS-HA), which can be first impregnated in the ECM, and then immobilized within the ECM by cross-linking of the adducts, e.g. the hydroxyphenyl or tyramine adducts, to form cross-links, e.g. dihydroxyphenyl or dityramine linkages, thereby producing a cross-linked HA macromolecular network, as shown schematically in FIG. 3, incorporated into the derived ECM. By cross-linking in situ within the ECM, the impregnated HA becomes entangled within the ECM and the resulting cross-linked HA macromolecular network becomes entrapped and interlocked therein. In addition, in situ cross-linking allows for the potential of direct cross-linking of HA bound adducts, e.g. tyramine, with tyrosine residues on native proteins within the derived ECM, to covalently bind the HA network to these proteins. Such proteins may be naturally occurring and retained in the derived ECM, or they can be separately incorporated to achieve a desired therapeutic effect. It has been shown that when approximately 5% of the dissacharides present in hyaluronan macromolecules are substituted with tyramine, this allows TS-HA to be discretely cross-linked (or gelled). The structure, and presumably the biological activity, of the cross-linked TS-HA is maintained, as evidenced by the positive binding of HA binding protein, as shown in FIG. 5 and described in more detail in the examples below.

Our data suggest that fascia lata ECM can be enriched with incorporated TS-HA by at least an order of magnitude compared to natural HA already present in fascia lata ECM, using diffusion methods. Moreover, TS-HA-enriched fascia has been shown to possess increased cell density compared to untreated fascia in a rat abdominal wall model (described in examples below). Data from the examples also suggest that fascia enriched with immobilized TS-HA is associated with less chronic inflammation than untreated fascia in the rat model. Together, these results indicate that incorporating a small concentration (1-2% tissue weight based on ECM) of high molecular weight HA into fascia lata ECM creates a milieu that enhances cellular infiltration and modulates inflammation—conditions favorable for graft incorporation and perhaps not unlike those found in fetal development. It is to be noted that up to ~1-2% loading (based on initial fascia tissue mass) has been obtained via the diffusion method mentioned above and described more fully hereinbelow. However, it is contemplated that higher TS-HA loading rates may be obtained through more aggressive loading techniques, for example via vacuum, centrifugation or electroporation. The above effects, combined with the tensile properties of fascia lata, support the use of fascia enriched with TS-HA for tendon-to-bone repair in general, and rotator cuff repair in particular. We expect that high-molecular-weight HA will reduce inflammation and promote cell migration into fascia, which would promote integration of the fascia patch with the underlying host tissues. As such the fascia patch would provide reinforcement to the tendon-to-bone repair during healing. This would diminish the occurrence of re-tearing following repair. The foregoing effects of combining HA with fascia lata to reinforce a tendon-to-bone repair will be particularly useful in rotator-cuff repair because of the high tensile forces seen in the shoulder joint during post-operative activities and the poor rates of biologic healing.

It is believed that HA-enrichment will enhance the host response to fascia such that augmenting rotator cuff repairs with an HA-enriched fascia patch will improve repair outcomes over conventional suture-only repair or augmentation with a patch comprised of only native fascia. It is further believed that enriching fascia ECM with exogenous high molecular weight hyaluronan (HA)—a molecule known to play a critical role in morphogenesis, wound repair, and modulating inflammation—may improve the fascia's ability to foster the formation of a functional tendon-bone bridge in rotator cuff repair by enhancing cellular infiltration and modulating inflammation.

Exogenous HA may be combined with fascia lata to produce an improved fascia lata ECM material. Fascia lata may be obtained, for example, from tissue banks as described above, as well as other sources. Fascia lata is typically supplied in decellularized form as a non-viable ECM material. It is a very dense material, and can be loaded with HA at ~1-2% of the total initial fascia tissue mass using diffusion methods. The added HA is distributed throughout the depth of the fascia scaffold, primarily around large fascicle bundles. As mentioned above, it may be possible to achieve greater loading via alternative and more aggressive techniques, including vacuum, centrifugation or electroporation.

As mentioned above, fascia lata often will be obtained from tissue banks and other commercial sources. These sources may apply special or even proprietary processing techniques to process the fascia lata before it is used. All of these techniques may have the effect of making the allograft fascia lata seem modestly foreign to the implantee's immune system. It is believed that incorporating small amounts of high-molecular-weight HA into the fascia lata (~1-2% of the total mass of ECM) will mask degraded or damaged proteins arising from processing and thus reduce the immune response of the implantee and enhance integration of the patch.

High-molecular weight non-cross-linked HA rapidly diffuses out of the fascia in vitro (e.g. within 1-72 hours). If HA diffuses rapidly out of the fascia, it would not be present to facilitate the beneficial effects described above in an implanted fascia lata (or other ECM) patch during the healing process. Therefore, the HA impregnated in the ECM is augmented to entrap it therein so that it will remain in the patch for at least a period of time during the implantee's healing process. Cross-linked, high-molecular-weight HA diffuses out of fascia lata ECM more slowly than uncross-linked HA of corresponding molecular weight. A cross-linked HA material that has been found particularly useful in this application is prepared by substituting tyramine moieties onto the HA chains and then linking tyramines to form dityramine linkages between HA chains, thus cross-linking or gelling the impregnated HA molecules to entrap and incorporate them into the fascia matrix. The preferred dityramine-cross-linked HA composition and chemistry is disclosed in U.S. Pat. Nos. 6,982,298, 7,368,502, and 7,465,766, the contents of all of which are incorporated herein by reference in their entirety.

Briefly, in accordance with the incorporated publications, a cross-linked HA or other polycarboxylate or polyamine macromolecular network can be prepared through covalent coupling of hydroxyphenyl-containing compounds, including but not limited to tyramine, through their primary amine groups to carboxyl groups on the long-chain macromolecules via a carbodiimide-mediated reaction. The hydroxyphenyl groups can be added to the macromolecules periodically or randomly along their length via a chemical reaction. Herein, the long-chain macromolecule preferably is HA, which has periodic carboxylic acid groups along its length and is preferred to facilitate a number of desirable effects (described above) beyond the use of un-augmented, derived ECM alone as a patch used to repair tissue defects. The hydroxyphenyl groups are provided as part of smaller molecules having primary amine groups that can be attached to the carboxyl carbon atoms of a carboxylic acid group on the HA macromolecules via the carbodiimide pathway. The reactions are described in detail in the publications incorporated above.

When substituting onto a HA molecule, suitable hydroxyphenyl-containing compounds include those having a free primary amine that can be used to modify scaffold materials having multiple or periodic $CO_2H$ groups, including tyrosine (2-amino-3-(4-hydroxyphenyl)propionic acid) and tyramine (tyrosamine or 2-(4-hydroxyphenyl)ethylamine).

The second step in preparing the cross-linked HA network is to link the hydroxyphenyl-substituted macromolecules via a dihydroxyphenyl linking structure. In this step hydroxyphenyl groups attached to different HA molecules are linked using a peroxide reagent in the presence of a peroxidase. Of note, some dihydroxyphenyl linking may occur between different hydroxyphenyl groups attached to the same molecule. Peroxidase in the presence of a dilute peroxide (preferably $H_2O_2$) is able to extract the phenolic hydroxyl hydrogen atom from hydroxyphenyl containing compounds (such as tyramine) leaving the phenolic hydroxyl oxygen with a single unshared electron, an extremely reactive free radical. The free radical isomerizes to one of the two equivalent ortho-position carbons and then two such structures dimerize to form a covalent bond effectively cross-linking the structures, which after enolizing generates a dihydroxyphenyl dimer, e.g. a dihydroxyphenyl linkage such as a dityramine linkage. Suitable peroxides include hydrogen peroxide. The peroxidase preferably is horseradish peroxidase (HRP). Alternatively, any other suitable enzyme or other agent can be used that is capable of generating free-radicals for cross-linking long-chain macromolecules that contain hydroxyphenyl groups. Considering the peroxidase enzyme in more detail, the peroxidase can either form hydroxyphenyl radicals required for cross-linking through interaction of hydroxyphenyl groups at the enzyme active site to directly create the desired radicals, or through generation of superoxide radicals, which then diffuse from the enzyme and interact with hydroxyphenyl groups to generate the desired radicals. Other compounds that have the potential to produce the same effect include any porphyrin containing compound, which includes the peroxidase family, hemoproteins, or the structurally related chlorin compounds. A number of other free radical initiators can also be used to crosslink the hydroxyphenyl-modified long-chain macromolecules, as described in detail in the publications incorporated above.

Returning to the augmented, derived ECM patches disclosed here, preferably the high-molecular-weight HA molecules to be incorporated into fascia lata or other suitable derived ECM have an average molecular weight of 250 kDa or greater, more preferably 500, 800 or 900 KDa or greater, more preferably 1 MDa or greater. Preferably, the tyramine-substitution rate on the HA molecules is about or less than five percent based on available substitution sites as disclosed in the aforementioned publications. It is desirable that tyramine-substitution onto the HA molecules be completed prior to impregnating the derived ECM. The substituted HA macromolecules of the desired molecular weight (preferably greater than 250 kDa as noted above) are then impregnated into the derived ECM via a suitable technique, such as passive diffusion as noted above. Subsequently, once the desired degree of TS-HA loading has been achieved (e.g. ~1-2%), the TS-HA-impregnated ECM is submerged in a solution including dilute hydrogen peroxide and the appropriate enzyme, e.g. HRP, to promote and facilitate the cross-linking reaction to generate dihydroxyphenyl (e.g. dityramine) linkages, to thereby interlock the impregnated HA macromolecules to produce an interlocked macromolecular network within the derived ECM. The submersion described here can be done either once the TS-HA-impregnated patch has been cut to the desired dimensions for the intended repair, or it can be done using a larger sheet of the material, which can be subsequently cut to size as needed for particular repairs.

The low tyramine-substitution rates described above allow HA to be discretely cross-linked while maintaining the majority of the HA molecules in their native conformation as evidenced by positive binding of hyaluronan binding protein (FIG. 5 described in the examples below). In addition to preserving the HA within the derived ECM, cross-linking as described above may inhibit or suppress the break-down of HA into molecules of relatively lower molecular weight.

Figure 4:
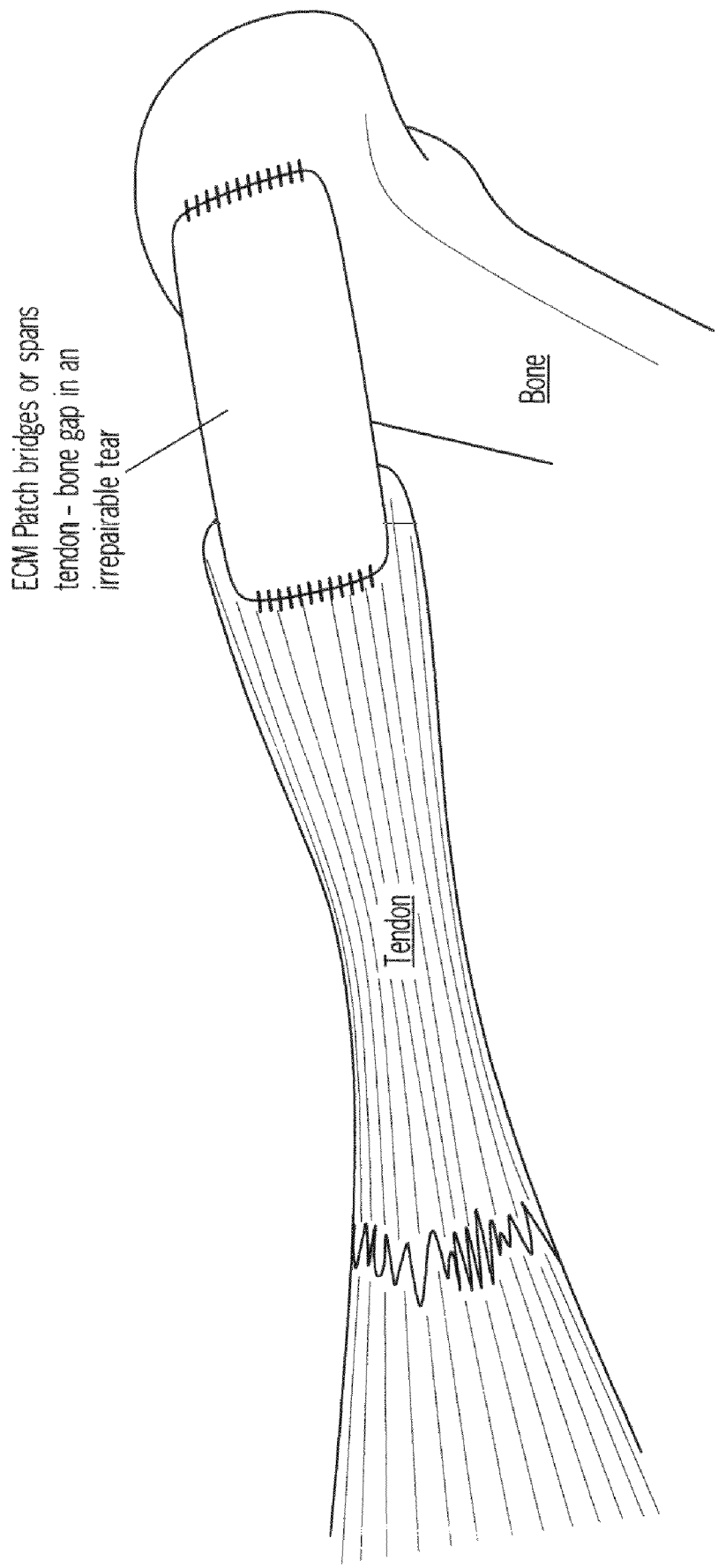
FIG. 4 is a schematic diagram of an extracellular matrix patch applied to repair a tissue defect between tendon and bone, bridging the gap between the tendon and bone in what would otherwise be an irreparable tear.

Thus far, the HA-augmented, derived ECM patch has been described, in conjunction with FIG. 1, as being applied over an extant surgical repair to attach or re-attach adjacent torn or separated tissues. As already explained, in this embodiment the patch serves to reinforce the surgical repair directly at the defect, with additional benefits realized as a result of incorporating the cross-linked macromolecular HA network in the patch. In an alternative embodiment, the patch disclosed herein also may be used as a bridging material in the case where the gap between separated or torn tissues, such as a tendon and the associated bone, is too large to repair conventionally, e.g. via direct suturing of the tissues. This can happen, for example, when there is no longer sufficient native tissue to close the tear or gap to bring opposed portions into contact for suturing. In one embodiment shown schematically in FIG. 4, a derived ECM patch, preferably augmented with impregnated and cross-linked HA as described above, is incorporated at the bone-tendon interface and fixed to both at its respective ends to bridge a gap that is otherwise too broad to be repaired conventionally. In this embodiment, the derived ECM patch will itself be integrated to both the bone and the tendon to act as a surrogate tendon-bone bridge, essentially repairing what traditionally would have been an irreparable gap or tear. Because fascia lata has properties very similar to tendon, it is already well suited to function in this role as the derived ECM of the patch. In addition, the entrapped (cross-linked) HA may promote integration of fascia lata to the bone and/or the tendon for reasons already discussed, which would facilitate the formation of a functional bridge.

While HA-impregnated fascia lata ECM has been described primarily with respect to rotator-cuff repairs, it will be appreciated that similar methods and materials as described here could also be adapted to other tendon-to-bone repairs, repairs of other connective tissues (such as ligaments or ligament-to-bone), soft-tissue repairs such as repair of lacerated or transferred muscles, as well as other repairs where a tissue defect or gap has occurred either through injury (such as a hernia) or surgically. In these cases, an HA-impregnated and incorporated (via cross-linking) derived ECM matrix, such as fascia lata, which can be prepared and supplied in the form of a patch having appropriate dimensions, can be applied over the defect (e.g. tear) either to form a tissue bridge that can be incorporated and remodeled via the implantee's own healing response into appropriate tissue to complete the repair, or to reinforce a surgical repair between the adjacent tissues while it heals. The presence of the high molecular weight HA trapped in the derived ECM should enhance the implantee's remodeling response to incorporate the derived ECM (e.g. fascia) into native tissues, and should suppress an inflammatory response that may interfere with healing.

While the derived ECM patch having impregnated and cross-linked HA can reinforce a repair site, the repair still may be prone to failure before biological healing occurs due to the sutures tearing through either the tendon or the bone, or through the ECM material (such as fascia lata) itself. Therefore, additional steps to induce functional integration at the repair site as quickly as possible, independent of sutures, are also desirable. Application of these steps may be desirable for repairs as depicted schematically in FIG. 1 and FIG. 4. For this purpose, it is believed that a gel made of tyramine-cross-linked collagen would be useful, for example, if injected between the ECM patch and the underlying tissue to be repaired, or between the implantee's tendon and bone or other separated tissue at the repair site, while suturing or after suturing is complete. Like HA, collagen is a polycarboxylate macromolecule capable of being substituted with tyramine or other hydroxyphenyl groups to facilitate dityramine (dihydroxyphenyl) linkage. Appropriate chemistry is described in detail in the publications incorporated above. The form of the collagen to be substituted with tyramine ranges from highly purified recombinant collagen to collagen that is a component of a tissue extract such as gelatin. To prepare a collagen gel suitable for this application, preferably collagen having an average molecular weight greater than 50 kDa, more preferably 100 kDa, is used. In this embodiment, tyramine-substituted collagen ("TS-collagen") is preferably cross-linked in situ between the opposed, sutured tissues allowing the TS-collagen to penetrate the opposed tissues as it cross-links. The TS-collagen would then cross-link (or gel) around the existing tissues and potentially cross-link to existing tyrosine residues within the tissues in a manner similar to the integration of TS-HA with proteins that may be present within fascia lata ECM, or within other derived ECM in the patch as described above. Use of TS-collagen in this manner may optimize the integration of the opposed tissues, serving as both a glue and potentially an inductive agent for repair.

While cross-linking of both HA and collagen described herein is preferably achieved via dityramine linkages as mentioned above and more fully described in the incorporated publications, it is contemplated that other dihydroxyphenyl linkages also may be used, e.g. via substitution and carbodiimide-mediated linking of suitable hydroxyphenyl adducts onto the HA or collagen chains. This is also further described in the incorporated publications. Direct incorporation of cells, biologics, and other active ingredients (such as drugs or other therapeutic compounds) into the TS-HA or TS-collagen macromolecular networks to induce healing is also contemplated as described in the incorporated publications.

While the present methods and patch are described primarily with respect to augmenting fascia lata ECM as the derived ECM as disclosed herein, it is to be recognized that the methods and compositions described herein may be applied analogously to incorporate TS-HA into other ECM materials besides fascia, such as dermis, small intestine submucosa, pericardium, or even other scaffold materials derived from polymeric biomaterials (i.e. animal-derived materials). In addition, the foregoing methods have been disclosed primarily in connection with impregnating and incorporating into the derived ECM HA macromolecules. The HA molecules are cross-linked by linking hydroxyphenyl, preferably tyramine, adducts attached to those molecules to generate an interlocked HA network that is retained in the derived ECM matrix. The resulting cross-linked ECM matrix accordingly diffuses out of the matrix more slowly, increasing the length of time during healing when it is present to produce beneficial effects. It is contemplated that other polycarboxylate or polyamine macromolecules other than HA, which lend themselves to substitution with hydroxyphenyl adducts followed by linkage via the above-described chemistry, may be incorporated into a derived ECM patch, such as a fascia lata patch, via analogous methods as disclosed for HA to produce corresponding desirable or therapeutic effects associated with those other macromolecules. Alternative (other than HA) polycarboxylate or polyamine macromolecules that may be impregnated into a derived-ECM matrix and then cross-linked via linkage of hydroxyphenyl adducts thereon may include molecules of or based on other glycosaminoglycans (such as heparin) and proteins (such as collagens). Such other polycarboxylate or polyamine macromolecules, which provide or may provide associated desirable effects, can be incorporated into the derived-ECM matrix via similar methods disclosed for HA herein and in the incorporated publications. In a further alternative, macromolecules already possessing native hydroxyphenyl side groups may be incorporated into a derived ECM matrix and then cross-linked to form dihydroxyphenyl linkages between native hydroxyphenyl side groups. In this case, the step of substituting hydroxyphenyl-containing groups onto the macromolecule can be omitted, because such groups are already present.

In summary, in a broad aspect there is disclosed a derived ECM matrix that incorporates a cross-linked macromolecular network interlocked within the derived ECM, which network includes polycarboxylate or polyamine macromolecules that have been substituted with hydroxyphenyl adducts and cross-linked via dihydroxyphenyl linkages. In a preferred aspect, the ECM matrix is fascia lata, preferably human fascia lata ECM, and the hydroxyphenyl-substituted polycarboxylate or polyamine molecules are tyramine-substituted HA molecules that have been cross-linked via dityramine linkages, to interlock a macromolecular HA network within the derived fascia lata matrix. The resulting matrix is cut or formed into dimensions suitable to be used as a patch, either to reinforce the surgical repair of a tissue defect or gap, or to repair the defect as in the case of a gap that is too broad for conventional suture-based repair. A patch composed of derived fascia lata ECM incorporating HA in the form of a macromolecular network that is cross-linked via dityramine linkages and thereby mechanically interlocked and retained within the ECM is contemplated to be particularly useful in repairing rotator-cuff tears, as well as other tendon-to-bone or connective tissue repairs.

Still further aspects and features of the invention will be apparent from the following examples, which are provided by way of illustration and not limitation.

Example 1

Acellularized human fascia lata was obtained from the Musculoskeletal Transplant Foundation (Edison, N.J.). Prior to shipment the fascia was processed according to a published procedure, as disclosed in WO/2006/101885, publication date of Sep. 28, 2006, which is incorporated by reference, with modifications, hereafter referred to as "standard pre-processing". Specifically, the modified process used by the Musculoskeletal Transplant Foundation comprised the following steps: (1) isolating fascia from a suitable donor; (2) processing the fascia including inspection for visual defects, trimming and soaking the tissue in phosphate buffered saline (PBS) and rinsing same with sterile PBS; (3) soaking the tissue in an antibiotic composition and rinsing same multiple times in sterile PBS; (4) processing the tissue by cutting the tissue to size; and (5) freezing the tissue in sterile PBS at −20° C. and shipping on dry ice.

HA was impregnated in fascia lata as follows. Approximately 4×4 cm samples of fascia lata were lyophilized for at least 24 hours. Following lyophilization, individual fascia samples were rehydrated in a 0.75% (w/v) TS-HA solution (corresponding to mass-volume percentage, such that the solution includes 0.75 g TS-HA per 100 ml) (—1.5 ml/cm$^2$) for 24 hours at 37° C. on a shaker. Molecular weight of TS-HA used was 900 kDa-1 MDa. The substitution rate of tyramine was ~5%. After impregnation of fascia with TS-HA, fascia was rinsed of excess TS-HA with high purity water for ~30 seconds and blotted two times per side. To cross-link the TS-HA, fascia was submerged into a 0.3% hydrogen peroxide solution for ~30 seconds and incubated overnight at 4° C. to allow the reaction to continue. Subsequently, fascia was rinsed of excess hydrogen peroxide with high purity water for ~30 seconds and lyophilized. Non-cross-linked samples were submerged in high purity water for ~30 seconds, incubated overnight at 4° C., rinsed, and lyophilized. Water controls were treated by incubation in high-purity water for 24 hours at 37° C. on a shaker, subjected to hydrogen peroxide, and subsequently lyophilized.

Fluorophore assisted carbohydrate electrophoresis (FACE) was used to quantify the HA content of the treated fascia samples, according to Calabro A. et al., Microanalysis of enzyme digests of hyaluronan and chondroitin/dermatan sulfate by fluorophore-assisted carbohydrate electrophoresis (FACE), Glycobiology 2000, 10(3), pp. 273-81; and Calabro A., Adaptation of FACE methodology for microanalysis of total hyaluronan and chondroitin sulfate composition from cartilage, Glycobiology 2000, 10(3): 283-293. Results are shown in TABLE 1.

TABLE 1

Fluorophore-assisted carbohydrate electrophoresis analysis (FACE) of HA content in diffusion-treated 4 × 4 cm fascia (STANDARD PRE-PROCESSING).

| Treatment group | Average TS-HA content (µg/mg) | Range (µg/mg) | Sample size |
|---|---|---|---|
| Water-treated | 0.07 ± 0.04 | 0.10-0.04 | 2 grafts, each represented by the average of 4 subsamples |
| 0.75% with cross-linking | 14.2 ± 6.8 | 4.4-26.9 | 8 grafts, each represented by the average of 2-5 subsamples |
| 0.75% without cross-linking | 14.6 ± 3.2 | 10.14-18.4 | 6 grafts, each represented by the average of 2-3 subsamples |

According to an alternative approach, fascia lata was pre-processed according to the method of the WO/2006/101885 publication, incorporated above (i.e., standard pre-processing), except that samples of fascia lata were 1×1 cm. Diffusion treatments of the fascia lata were evaluated based on TS-HA solutions that were 0.5, 0.75, or 1% (w/v). FACE was used to quantify the HA content of the treated fascia samples, according to the above-mentioned Calabro publications. Results are shown in TABLE 2.

TABLE 2

Fluorophore-assisted carbohydrate electrophoresis analysis (FACE) of HA content in diffusion-treated 1 × 1 cm fascia (STANDARD PRE-PROCESSING).

| Treatment group | Average TS-HA content (µg/mg) | Range (µg/mg) | Sample size |
|---|---|---|---|
| 0.5% with cross-linking | 2.5 ± 1.4 | 0.6-5.1 | 15 |
| 0.75% with cross-linking | 6.9 ± 3.0 | 2.2-10.8 | 11 |
| 1% with cross-linking | 12.1 ± 4.1 | 8.3-17.3 | 5 |

According to another alternative approach, fascia lata was preprocessed according to the method of the WO/2006/101885 publication, incorporated above, with modifications. Specifically, bulk fascia lata was prepared and shipped (hereafter referred to as "bulk pre-processing"). Bulk fascia is fascia that is processed according to WO/2006/101885, except that tissue is subjected to only 4 hours of the antibiotic soak rather than the full 24 hours. Upon receipt of shipped bulk fascia lata, the antibiotic soak process was continued in house by subjecting the fascia to an additional 20 hours soak prior to freezing and lyophilization. Additionally, bulk fascia was cleaned in house of excess loose connective tissue and fat. Bulk fascia lata (~4×4 cm) was then treated using 0.75% (w/v) TS-HA solution. FACE was used to quantify the HA content of the treated fascia samples, according to the above-mentioned Calabro publications. Results are shown in TABLE 3.

TABLE 3

Fluorophore-assisted carbohydrate electrophoresis analysis (FACE) of HA content in diffusion-treated 4 × 4 cm fascia (BULK PRE-PROCESSING).

| Treatment group | Average TS-HA content (µg/mg) | Range (µg/mg) | Sample size |
|---|---|---|---|
| 0.75% with cross-linking | 10.4 | 7.6-13.2 | 2 grafts, each represented by the average of 6 subsamples |

According to a further alternative approach, fascia lata was preprocessed according to the method of the WO/2006/

101885 publication, incorporated above, with modifications. Specifically, bulk fascia that was not subjected to lyophilization prior to TS-HA impregnation was treated (hereafter referred to as "bulk, not lyophilized, pre-processing"). Instead, fascia was kept hydrated in PBS at 4° C. until subjected to TS-HA treatment. Fascia (~4×4 cm) was treated using 0.75% (w/v) and 2% (w/v) TS-HA solutions. FACE was used to quantify the HA content of the treated fascia samples, according to the above-mentioned Calabro publications. Results are shown in TABLE 4.

TABLE 4

Fluorophore-assisted carbohydrate electrophoresis analysis (FACE) of HA content in diffusion-treated 4 × 4 cm fascia (BULK, NOT LYOPHILIZED, PRE-PROCESSING).

| Treatment group | Average TS-HA content (µg/mg) | Range (µg/mg) | Sample size |
|---|---|---|---|
| 0.75% with cross-linking | 2.0 | NA | 1 graft, each represented by the average of 12 subsamples |
| 2% with cross-linking | 4.9 | NA | 1 graft, each represented by the average of 6 subsamples |

In an additional analysis method, TS-HA treated fascia samples (1×1 cm, diffusion, standard pre-processing) were rehydrated in 0.2 ml of saline for 5 minutes and embedded in Tissue-Tek® OCT compound. Five micron longitudinal frozen sections were cut and stained with biotinylated HA binding protein (HABP, Calbiochem, San Diego, Calif.) and Alexa Fluor® 488 conjugated streptavidin (Molecular Probes, Carlsbad, Calif.) to visualize TS-HA distribution in the tissue. HABP staining demonstrated TS-HA incorporation throughout the depth of the tissue, primarily around large fascicle bundles (FIG. 5). The arrow in FIG. 5B denotes staining of TS-HA. It is desirable that the added HA is distributed throughout the fascia, rather than being layered in high concentration on the surface, to promote more uniform benefits of HA incorporation, such as suppression of an inflammatory response. Further, the binding of HABP demonstrates that the TS-HA remains biologically active after cross-linking.

Example 2

A method for impregnation of fascia lata with HA based on vacuum is as follows. Fascia lata, pre-processed according to either standard or bulk methods as described in Example 1 above, was lyophilized for at least 24 hours. Following lyophilization, fascia was cut into 3 cm diameter samples and rehydrated in high purity water for ~10 minutes. Individual fascia lata samples were then mounted onto the platform of a modified Millipore Steriflip® filtration system. The top vessel was filled with ~10 ml of TS-HA solution and secured to the filtration system. Vacuum was applied and the TS-HA solution was pulled through the fascia lata. This was repeated to increase the number of passes of solution through the fascia lata. The concentrations evaluated were 0.5, 0.75, 1% (w/v), and increasing concentrations. FACE was used to quantify the HA content of the treated fascia samples, according to the above-mentioned Calabro publications. Results are shown in TABLE 5.

TABLE 5

Fluorophore-assisted carbohydrate electrophoresis analysis (FACE) of HA content in vacuum-treated 3 cm diameter fascia.

| Treatment group | Fascia pre-processing | Average TS-HA content (µg/mg) | Range (µg/mg) | Sample size |
|---|---|---|---|---|
| 0.5%, 8 passes, with cross-linking | Bulk | 1.9 ± 0.5 | 1.4-2.3 | 3 grafts, each represented by the average of 2 subsamples |
| 0.75%, 1 pass, with cross-linking | Bulk | 3.0 ± 1.0 | 1.8-4.5 | 6 |
| 1%, 2 passes, with cross-linking | Bulk | 12.6 ± 5.1 | 6.7-16 | 3 |
| 1%, 8 passes, with cross-linking | Bulk | 16.0 ± 8.4 | 7.4-24.2 | 3 |
| Increasing concentrations, 2 passes per concentration, with cross-linking | Standard | 1.4 ± 0.8 | 0.7-2.3 | 3 grafts, each represented by the average of 2 subsamples |

Example 3

A method for impregnation of fascia lata with HA based on centrifugation is as follows. Fascia lata, pre-processed according to the standard method as described in Example 1 above, was received lyophilized, cut into 1 cm diameter samples, and rehydrated in high purity water for ~10 minutes. Individual fascia samples were placed into a centrifugal filter device corresponding to a Millipore Centricon® tube and covered with 1.5 ml of HA (for this example, not TS-HA) solution. The Centricon tube was then centrifuged at 5000 g for ~1 hour. The solution "filtrate" was placed back into the Centricon tube and the centrifugation was repeated once more. The concentration evaluated was increasing concentrations (0.05→0.1→0.2→0.5% (w/v)). To visualize HA distribution in fascia samples, the samples were rehydrated in 0.2 ml of saline for 5 minutes and embedded in Tissue-Tek® OCT compound. Five micron longitudinal frozen sections were cut and stained with biotinylated HA binding protein (HABP, Calbiochem, San Diego, Calif.) and Alexa Fluor® 488 conjugated streptavidin (Molecular Probes, Carlsbad, Calif.). HABP staining demonstrated HA incorporation throughout the depth of the tissue, similar to FIG. 5.

Example 4

An experiment was conducted to evaluate the host response to TS-HA enriched fascia ECM in a rat abdominal wall model.

Experimental Design. Acellularized human fascia lata was cut into 1×1 cm samples and distributed into three treatment groups: TS-HA with cross-linking, HA without cross-linking, or untreated controls. Samples were treated in a similar manner as described in Example 1. At surgery, fascia grafts were rehydrated and implanted into a partial-thickness defect of the anterior sheath of 6 rats, n=2 per group, as described in the following section. Additional details are provided in the following reference: Valentin J E et al., Extracellular matrix bioscaffolds for orthopaedic applications. A comparative histologic study. J. Bone Joint Surg.[Am.] 2006; 88(12):2673-86. At four weeks, rats were euthanized and the graft and surrounding muscle were harvested for histology. Cell density within the graft was quantified using image processing techniques detailed below. Inflammation was qualitatively assessed by a board-certified pathologist.

Rat Abdominal Wall Defect Model. Adult, male Lewis rats (450-600 gm) were used. Rats were anesthetized and prepared for sterile surgery. Via a ventral midline incision, a partial-thickness 1×1 cm defect was created in the anterior sheath adjacent to the linea alba. The anterior sheath was removed and the underlying rectus muscle, transversalis fascia, and peritoneum were left intact. A 1×1 cm fascia ECM patch was rehydrated in saline for ten minutes and then secured into the defect using four corner sutures of 5-0 Prolene. Securing the fascia theoretically allowed the ECM patch to be subjected to the mechanical forces delivered by the adjacent native abdominal wall musculature. The skin incision was closed and the animals were allowed to recover from anesthesia under a heating lamp before being returned to individual cages for the duration of the study.

Histologic Processing and Analysis. At euthanasia, the fascia graft and surrounding muscle were harvested, fixed in 4% paraformaldehyde and processed routinely for paraffin embedding. Five micron thick longitudinal sections of each sample were cut and stained with hematoxylin and eosin (H&E). RGB images of the H&E sections were acquired using a Retiga 2000R CCD digital camera (1600×1200 pixel, Q-Imaging, Burnaby, B.C., Canada) attached to a Leica DM 4000 upright microscope (Heidelberg, Germany) fitted with a 10× objective. Image acquisition was fully automated using an X, Y, Z-motorized stage (Prior Scientific, Rockland, Mass.) managed by Objective Imaging's Oasis 4i controller (Kansasville, Mich.) and Image-Pro 6.0 software (Media Cybernetics, Silver Spring, Md.). Images were captured of the entire length and width of each sample and knitted into a single montage. Image-Pro was used to count hematoxylin stained nuclei and determine respective tissue area on three sections per rat. Inflammation was qualitatively rated by a board-certified pathologist on one section per rat.

Figure 6:
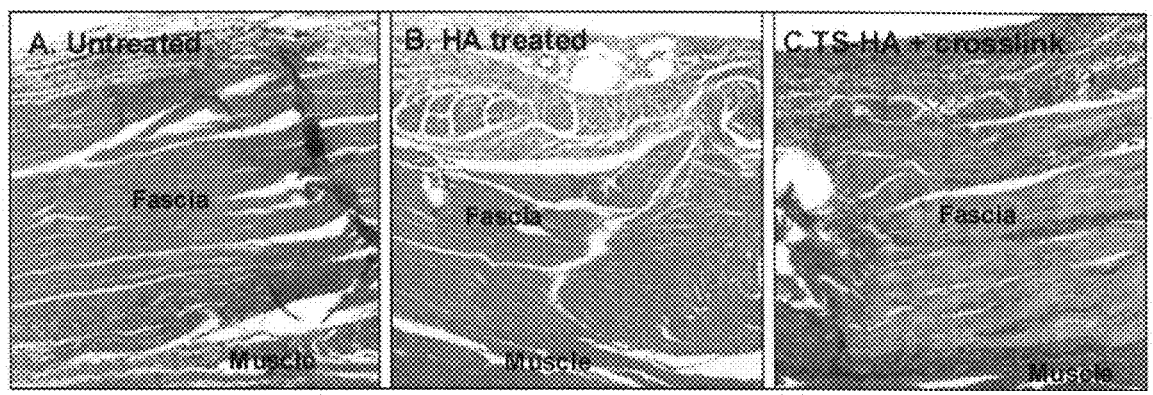
FIG. 6 is a series of three photographs showing representative histologic sections of fascia extracellular matrix grafts following implantation in the rat abdominal wall model for four weeks (hematoxylin & eosin staining, 10×), wherein the fascia was (A) untreated, (B) HA-treated, and (C) TS-HA treated followed by cross-linking, as described in Example 4.

Results: Cell Number in Fascia ECM. At four weeks the histologic appearance of the fascia in all groups characteristically exhibited a highly cellular periphery and fewer cells in the central portion of the graft (FIG. 6). The fascia graft and underlying muscle layers are denoted (FIG. 6). Increased cellularity was present within the fascia in the HA treated groups (FIG. 6B-C) compared to untreated fascia (FIG. 6A). Cells were counted from a manually selected region of interest on the montaged images that included the entire fascia graft (~4 mm$^2$). The cell densities are shown in TABLE 6. Because of the small sample size in this study, the six measures from the two rats for each group were used for preliminary statistical comparisons using analysis of variance. At four weeks, cell density within TS-HA treated grafts (2859±295 cells/mm$^2$) was significantly greater than untreated grafts (2102±545 cells/mm$^2$) (p=0.02). Cell density within uncross-linked HA-treated grafts (2724±662 cells/mm$^2$) may also prove to be different from untreated grafts (p=0.06) when assessed in a larger sample size.

TABLE 6

Cell density within the fascia grafts after 4 weeks implantation in a rat abdominal wall model.

| Treatment Group | Rat Number | Section #1 cells/mm$^2$ | Section #2 cells/mm$^2$ | Section #3 cells/mm$^2$ | Average per rat | SD per rat | Average per group (n = 2 rats) |
|---|---|---|---|---|---|---|---|
| Water control | 1 | 2324 | 1537 | 1972 | 1944 | 394 | 2102 |
|  | 2 | 2998 | 2213 | 1568 | 2260 | 716 |  |
| TS-HA with cross-linking | 3 | 3255 | 2959 | 3109 | 3108 | 148 | 2859 |
|  | 4 | 2664 | 2492 | 2677 | 2611 | 103 |  |
| HA without cross-linking | 5 | 3752 | 2887 | 3155 | 3265 | 443 | 2724 |
|  | 6 | 2089 | 2111 | 2350 | 2183 | 145 |  |

Results: Chronic Inflammation in Fascia ECM. Slides from each of the six rats were blinded and ranked on two occasions separated by a period of two months by a board-certified pathologist. Slides were ranked for "chronic inflammation" in and around the graft, as defined primarily by the presence of lymphocytes and plasma cells. The rankings are shown in TABLE 7. There was variability in the degree of inflammation observed in the HA treatment without cross-linking group. Based on these rankings it is suggested that TS-HA treatment plus cross-linking is associated with the least chronic inflammation of the three groups. However, it should be noted that the evaluation was limited by an inability to distinguish lymphocytes from macrophages with certainty. Note that Rat 5 was considered to have the highest degree of inflammation (TABLE 7) and the greatest number of cells (TABLE 6) whereas Rat 4 had the least inflammation but still a high number of cells. This outcome suggests that the cell types making up the total cell counts in each group might be different and probably reflects an attempt by the pathologist to distinguish chronic inflammation (lymphocytes and plasma cells) from macrophages and stromal cells in the rankings.

TABLE 7

Chronic inflammation ranking. Slides were ranked for lymphocytes and plasma cells in and around the fascia graft; Rankings were repeated twice, 1 = most, 6 = least.

| Treatment Group | Rat Number | Inflammation Rank (2 repeats) |
|---|---|---|
| Water control | 1 | 2, 2 |
|  | 2 | 3, 4 |
| TS-HA with cross-linking | 3 | 4, 3 |
|  | 4 | 6, 6 |
| HA without cross-linking | 5 | 1, 1 |
|  | 6 | 5, 5 |

Discussion. These data are important because they demonstrate use of the rat abdominal wall model to assess host response to fascia ECM scaffolds. Further, these data suggest that HA treatment will increase the total cell number in fascia ECM compared to untreated fascia. These data also provide the basis for the hypothesis that fascia enriched with TS-HA plus cross-linking will be associated with fewer lymphocytes and plasma cells but a similar number of macrophages and giant cells compared to fascia enriched with TS-HA without cross-linking or fascia treated with water. Finally, these data demonstrate the need for positive identification of cell types in order to definitively interpret the effect of HA treatment on host response.

Example 5

An experiment was conducted to evaluate the in vitro release of TS-HA from TS-HA enriched fascia ECM.

Experimental Design. Standard pre-processed human fascia lata (4×4 cm) was treated with TS-HA with or without cross-linking using the diffusion methods described in Example 1 (n=2 per experimental group). From each graft, a 0.8×1 cm sample was cut. Fascia samples were rehydrated in 1.2 ml of PBS and incubated for 72 hours at 37° C. on a shaker. After the 72 hours, fascia pieces were lyophilized and TS-HA content was measured with FACE. The initial TS-HA content of the incubated samples was estimated from the average of several small pieces sampled over the entire 4×4 cm graft that were not incubated, using FACE according to the above-mentioned Calabro publications.

Results: In Vitro Release of TS-HA from TS-HA Treated Fascia. The average percent release of TS-HA after 72 hours in PBS from TS-HA treated fascia with cross-linking was 73% (n=2, with results of 70.1% and 76.6% release). The average percent release of TS-HA after 72 hours in PBS from TS-HA treated fascia without cross-linking was 81% (n=2 with, results of 82.8% and 78.5% release).

Discussion. These data suggest that cross-linking will slow the release of TS-HA from fascia ECM compared to without cross-linking. Additional experiments and a greater sample size are desirable to determine if longer cross-linking time (submersion in peroxide solution with HRP) will further entrap the TS-HA molecules in the fascia ECM and slow their release to an even greater extent.

Although the above-described embodiments constitute the preferred embodiments, it will be understood that various changes or modifications can be made thereto without departing from the spirit and the scope of the present invention as set forth in the appended claims.

What is claimed is:

1. A composition comprising a derived extracellular matrix having incorporated therein a macromolecular network comprising polycarboxylate, polyamine or polyhydroxyphenyl macromolecules that have been cross-linked via dihydroxyphenyl linkages, said macromolecular network being interlocked within said derived extracellular matrix.

2. The composition of claim 1, said derived extracellular matrix being selected from the group consisting of fascia lata, dermis, small intestinal submucosa and pericardium.

3. The composition of claim 1, said derived extracellular matrix comprising fascia lata.

4. The composition of claim 3, said fascia lata being non-viable fascia lata.

5. The composition of claim 3, said macromolecules comprising hyaluronan macromolecules.

6. The composition of claim 5, said hyaluronan macromolecules having tyramine adducts substituted thereon, said dihydroxyphenyl linkages comprising dityramine linkages.

7. The composition of claim 6, said hyaluronan macromolecules having a tyramine-substitution rate of about or less than 5% based on available substitution sites on said hyaluronan macromolecules.

8. The composition of claim 3, comprising 1-2 weight percent hyaluronan macromolecules based on the weight of said fascia lata.

9. The composition of claim 5, said hyaluronan macromolecules having an average molecular weight of 900 KDa or greater.

10. The composition of claim 3, said fascia lata being viable fascia lata.

11. A method of making an implantable composition, comprising:
a) impregnating a derived extracellular matrix with hyaluronan macromolecules that have hydroxyphenyl side groups substituted thereon; and
b) thereafter reacting said hydroxyphenyl side groups to form dihydroxyphenyl linkages, thereby incorporating a cross-linked macromolecular network of hyaluronan that is interlocked within said derived extracellular matrix.

12. The method of claim 11, said derived extracellular matrix being selected from the group consisting of fascia lata, dermis, small intestinal submucosa and pericardium.

13. The method of claim 11, said hydroxyphenyl side groups comprising tyramine side groups, said dihydroxyphenyl linkages comprising dityramine linkages.

14. The method of claim 13, said hyaluronan macromolecules having a tyramine-substitution rate of about or less than 5% based on available substitution sites on said hyaluronan macromolecules.

15. The method of claim 11, said derived extracellular matrix comprising fascia lata, said fascia lata being impregnated by said hyaluronan macromolecules at a loading rate of 1-2 weight percent based on the weight of said fascia lata.

16. The method of claim 11, said hyaluronan macromolecules having an average molecular weight of 250 kDa or greater.

17. The method of claim 11, said derived extracellular matrix being non-viable derived extracellular matrix.

18. The method of claim 11, said impregnating step comprising lyophilizing said extracellular matrix and rehydrating the same in a solution comprising tyramine-substituted hyaluronan to diffuse said tyramine-substituted hyaluronan into said extracellular matrix.

19. The method of claim 11, said impregnating step comprising lyophilizing said extracellular matrix, rehydrating the same, and applying a vacuum thereto such that a solution comprising tyramine-substituted hyaluronan is drawn through said extracellular matrix.

20. The method of claim 11, said impregnating step comprising lyophilizing said extracellular matrix, rehydrating the same, covering said extracellular matrix with a solution comprising tyramine-substituted hyaluronan, and subjecting said extracellular matrix to centrifugation.

21. The method of claim 11, said reacting step comprising submerging said derived extracellular matrix in a solution of about 0.3% hydrogen peroxide for about 30 seconds and incubating the extracellular matrix at 4° C. to cross-link the HA within the extracellular matrix.

22. A method of reinforcing a tissue repair, or repairing a tissue defect or gap, comprising:
a) providing a patch comprising a derived extracellular matrix having impregnated therein polycarboxylate, polyamine or polyhydroxyphenyl macromolecules that have hydroxyphenyl side groups thereon, said hydroxyphenyl side groups being cross-linked to form dihydroxyphenyl linkages, thereby incorporating in said extracellular matrix a cross-linked macromolecular network of said macromolecules that is interlocked within said extracellular matrix;
b) identifying a tissue defect or gap in animal or human tissue in vivo; and c) applying said patch to repair said tissue defect or gap, or to reinforce a repair thereof.

23. The method of claim 22, said derived extracellular matrix comprising fascia lata, said macromolecules comprising hyaluronan macromolecules.

24. The method of claim 23, said patch comprising 1-2 weight percent hyaluronan macromolecules based on the weight of said fascia lata.

25. The method of claim 23, said hydroxyphenyl side groups comprising tyramine groups, said dihydroxyphenyl linkages comprising dityramine linkages, said tyramine groups being substituted on said hyaluronan macromolecules at a substitution rate of about or less than 5% based on available substitution sites.

26. The method of claim 22, comprising suturing said tissue defect or gap closed to repair the same, and applying said patch over the sutured defect or gap to reinforce it.

27. The method of claim 22, further comprising injecting tyramine-substituted collagen between said patch and host tissues surrounding said tissue defect or gap and cross-linking said tyramine substituted collagen to obtain a collagen gel.

28. A patch for reinforcing a tissue repair, or repairing a tissue defect or gap, comprising the composition of claim 6.

* * * * *